United States Patent
Parham et al.

(10) Patent No.: US 10,622,567 B2
(45) Date of Patent: Apr. 14, 2020

(54) MATERIALS FOR ORGANIC ELECTROLUMINESCENT DEVICES

(71) Applicant: Merck Patent GmbH, Darmstadt (DE)

(72) Inventors: Amir Hossain Parham, Franfurt am Main (DE); Christof Pflumm, Darmstadt (DE); Anja Jatsch, Frankfurt am Main (DE); Thomas Eberle, Landau (DE); Jonas Valentin Kroeber, Frankfurt am Main (DE)

(73) Assignee: Merck Patent GmbH, Darmstadt (DE)

(*) Notice: Subject to any disclaimer, the term of this patent is extended or adjusted under 35 U.S.C. 154(b) by 853 days.

(21) Appl. No.: 14/413,878

(22) PCT Filed: Jun. 12, 2013

(86) PCT No.: PCT/EP2013/001724
§ 371 (c)(1),
(2) Date: Jan. 9, 2015

(87) PCT Pub. No.: WO2014/008967
PCT Pub. Date: Jan. 16, 2014

(65) Prior Publication Data
US 2015/0295186 A1    Oct. 15, 2015

(30) Foreign Application Priority Data
Jul. 10, 2012  (EP) .................... 12005099

(51) Int. Cl.
| | | |
|---|---|---|
| *H01L 51/00* | (2006.01) |
| *C07D 487/16* | (2006.01) |
| *C07D 498/06* | (2006.01) |
| *C07D 471/06* | (2006.01) |
| *C07D 471/16* | (2006.01) |
| *C07D 487/06* | (2006.01) |
| *C07D 519/00* | (2006.01) |
| *C07D 498/16* | (2006.01) |
| *C07D 513/06* | (2006.01) |
| *C07D 513/16* | (2006.01) |
| *H05B 33/20* | (2006.01) |
| *C09K 11/06* | (2006.01) |
| *H01L 51/50* | (2006.01) |

(52) U.S. Cl.
CPC ........ *H01L 51/0072* (2013.01); *C07D 471/06* (2013.01); *C07D 471/16* (2013.01); *C07D 487/06* (2013.01); *C07D 487/16* (2013.01); *C07D 498/06* (2013.01); *C07D 498/16* (2013.01); *C07D 513/06* (2013.01); *C07D 513/16* (2013.01); *C07D 519/00* (2013.01); *C09K 11/06* (2013.01); *H01L 51/0071* (2013.01); *H01L 51/0073* (2013.01); *H01L 51/0074* (2013.01); *H05B 33/20* (2013.01); *C09K 2211/1011* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1074* (2013.01); *C09K 2211/1088* (2013.01); *C09K 2211/1092* (2013.01); *H01L 51/5012* (2013.01); *H01L 51/5016* (2013.01); *H01L 51/5056* (2013.01); *H01L 51/5088* (2013.01); *H01L 51/5096* (2013.01)

(58) Field of Classification Search
None
See application file for complete search history.

(56) References Cited

U.S. PATENT DOCUMENTS

| | | |
|---|---|---|
| 8,785,636 B2 | 7/2014 | Parham et al. |
| 9,133,119 B2 | 9/2015 | Parham et al. |
| 2012/0068170 A1 | 3/2012 | Pflumm et al. |
| 2012/0202997 A1* | 8/2012 | Parham ............... C07D 471/04 544/180 |

FOREIGN PATENT DOCUMENTS

| | | |
|---|---|---|
| DE | 102009023155 A1 | 12/2010 |
| EP | 2182040 A2 | 5/2010 |
| JP | H05107784 A | 4/1993 |
| JP | H11339868 A | 12/1999 |
| JP | 2012234873 A | 11/2012 |
| KR | 10-2012-0054154 * | 5/2012 |
| WO | WO-2006033563 A1 | 3/2006 |
| WO | WO-2008066358 A1 | 6/2008 |
| WO | WO-2011/042107 A2 | 4/2011 |
| WO | WO-2011/088877 A1 | 7/2011 |
| WO | WO-2012/067415 A2 | 5/2012 |

OTHER PUBLICATIONS

Machine English translation of KR 10-2012-0054154. Nov. 3, 2017.*
Machine English translation of Hikime et al. (JP 2012-234873 A). May 7, 2018.*
Plant et al. (J. Chem. Soc. 1950, p. 2127).*
Chinese office action dated Nov. 19, 2015 in the Chinese corresponding application No. 201380036876.5.
International Search Report for PCT/EP2013/001724 dated Jan. 22, 2014.

* cited by examiner

*Primary Examiner* — Jay Yang
(74) *Attorney, Agent, or Firm* — Faegre Drinker Biddle & Reath LLP

(57) ABSTRACT

The present invention relates to compounds according to formula (1) and formula (2), said compounds being suitable for use in electronic devices, in particular organic electroluminescent devices.

12 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2013/001724, filed Jun. 12, 2013, which claims benefit of European Application No. 12005099.2, filed Jul. 10, 2012, both of which are incorporated herein by reference in their entirety.

The present invention relates to materials which are suitable for use in electronic devices, in particular in organic electroluminescent devices.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, there is still a need for improvement, for example with respect to efficiency, operating voltage and lifetime, in the case of OLEDs, in particular also in the case of OLEDs which exhibit triplet emission (phosphorescence). This applies, in particular, to OLEDs which emit in the relatively short-wave region.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials may thus also result in significant improvements in the OLED properties. There is also still a need for improvement in the case of these materials for fluorescent OLEDs.

The object of the present invention is the provision of compounds which are suitable for use in a fluorescent or phosphorescent OLED, in particular a phosphorescent OLED, for example as matrix material or as hole-transport/electron-blocking material or exciton-blocking material.

Surprisingly, it has been found that certain compounds described in greater detail below achieve this object and result in improvements in the organic electroluminescent device, in particular with respect to the lifetime, the efficiency and/or the operating voltage. This applies, in particular, in the case of use of the compounds according to the invention as matrix material, but also in the case of use as hole-transport material or hole-injection material. The present invention therefore relates to these materials and to organic electroluminescent devices which comprise compounds of this type.

WO 2011/042107 discloses bridged carbazole derivatives which are substituted by triazine or other electron-deficient heteroaryl groups, where the substitution by the electron-deficient heteroaryl groups is essential. These compounds are described, in particular, as matrix materials for phosphorescent emitters. Compounds without this substitution pattern are not disclosed.

WO 2011/088877 discloses bridged carbazole derivatives which are substituted by diarylamino, triarylamino or carbazole groups, where the substitution by these groups is essential. Compounds without this substitution pattern are not disclosed.

Surprisingly, it has been found that the use of the compounds according to the invention in organic electroluminescent devices results in good electronic properties.

The present invention therefore relates to a compound of the following formula (1) or (2),

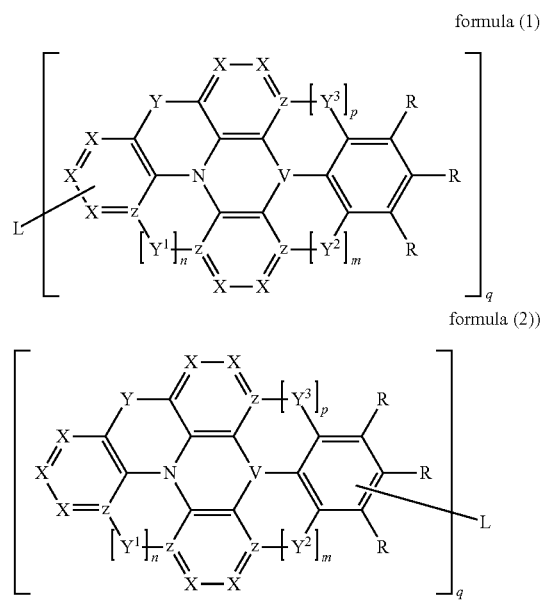

formula (1)

formula (2)

where the following applies to the symbols and indices used:

V is on each occurrence, identically or differently, N, P or P=O;

X is on each occurrence, identically or differently, CR or N; or X stands for C if a group L is bonded to this group X;

Y, $Y^1$, $Y^2$, $Y^3$ is on each occurrence, identically or differently, a single bond or $C(R^1)_2$, $NR^1$, O, S, C=O, C=$NR^1$, C=$C(R^1)_2$, $Si(R^1)_2$, $BR^1$, $PR^1$, P(=O)$R^1$, SO, $SO_2$; with the proviso that Y and $Y^1$ do not simultaneously stand for a single bond and that $Y^2$ and $Y^3$ do not simultaneously stand for a single bond;

Z is on each occurrence, identically or differently, CR or N; or Z stands for C if a group $Y^1$ or $Y^2$ or $Y^3$ is bonded to this group Z;

L is, identically or differently, R if q=1 or is a di-, tri-, tetra-, penta- or hexavalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, which may be substituted by in each case one or more radicals $R^2$, where in each case one or more non-adjacent $CH_2$ groups may be replaced by —$R^2$C=$CR^2$—, —C≡C—, $Si(R^2)_2$, C=O, C=$NR^2$, P(=O)$R^2$, S=O, $SO_2$, —O—, —S— or —$CONR^2$— and where one or more H atoms may be replaced by D, F, Cl, Br, I, CN or $NO_2$, or a di-, tri-, tetra-, penta- or hexavalent aromatic ring system having 5 to 40, aromatic ring atoms, which may be substituted by one or more radicals $R^2$, or heteroaromatic ring system having 5 to 60 aromatic ring atoms, which contains, as heteroaryl groups, exclusively sulfur-containing or oxygen-containing heteroaryl groups and which may be substituted by one or more radicals $R^2$, or $P(R^2)_{3-r}$, $P(=O)(R^2)_{3-r}$, $C(R^2)_{4-r}$, $Si(R^2)_{4-r}$, $N(Ar)_{3-r}$, where r stands for 2, 3 or 4, with the proviso that r is not greater than the maximum valence of L; or L is a chemical bond, in which case q=2; the valence of the group L=q+1 here;

n, m, p is on each occurrence, identically or differently, 0 or 1, where n=0 or m=0 or p=0 means that the corresponding group $Y^1$ or $Y^2$ or $Y^3$ respectively is not present and that a group R is bonded to the corresponding carbon atom instead of $Y^2$ or $Y^3$;

q is 1, 2, 3, 4, 5 or 6;

R, $R^1$ is selected on each occurrence, identically or differently, from the group consisting of H, D, F, Cl, Br, I, CN, $NO_2$, C(=O)Ar, C(=O)$R^2$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, C≡C, Si($R^2$)$_2$, C=O, C=N$R^2$, P(=O)($R^2$), SO, $SO_2$, $NR^2$, O, S or CON$R^2$ and where one or more H atoms may be replaced by D, F, Cl, Br, I, CN or $NO_2$, an aromatic ring system having 6 to 60 aromatic ring atoms, which may in each case be substituted by one or more radicals $R^2$, a heteroaromatic ring system having 5 to 60 aromatic ring atoms, which contains, as heteroaryl groups, sulfur-containing or oxygen-containing heteroaryl groups and which may be substituted by one or more radicals $R^2$, an aryloxy or heteroaryloxy group having 5 to 60 aromatic ring atoms, which may be substituted by one or more radicals $R^2$, or an aralkyl or heteroaralkyl group having 5 to 60 aromatic ring atoms, which may be substituted by one or more radicals $R^2$, where two substituents $R^1$ which are bonded in the same group Y may optionally form a mono- or polycyclic, aliphatic, aromatic or heteroaromatic ring system with one another, which may be substituted by one or more radicals $R^2$; furthermore, two adjacent radicals R may form a condensed-on benzo ring, which may be substituted by one or more radicals $R^2$; the group R in formula (2) is not present if the group L is bonded to the corresponding carbon atom;

$R^2$ is selected on each occurrence, identically or differently, from the group consisting of H, D, F, Cl, Br, I, CN, $NO_2$, C(=O)Ar, C(=O)$R^3$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, C≡C, Si($R^3$)$_2$, C=O, C=N$R^3$, P(=O)($R^3$), SO, $SO_2$, $NR^3$, O, S or CON$R^3$ and where one or more H atoms may be replaced by D, F, Cl, Br, I, CN or $NO_2$, an aromatic ring system having 5 to 60 aromatic ring atoms, which may in each case be substituted by one or more radicals $R^3$, an aryloxy or heteroaryloxy group having 5 to 60 aromatic ring atoms, which may be substituted by one or more radicals $R^3$, or an aralkyl or heteroaralkyl group having 5 to 60 aromatic ring atoms;

Ar is on each occurrence, identically or differently, an aromatic or heteroaromatic ring system having 5-30 aromatic ring atoms, which may be substituted by one or more non-aromatic radicals $R^3$; two radicals Ar which are bonded to the same P atom may also be bridged to one another here by a single bond or a bridge selected from N($R^3$), C($R^3$)$_2$, O or S;

$R^3$ is selected from the group consisting of H, D, F, CN, an aliphatic hydrocarbon radical having 1 to 20 C atoms or an aromatic ring system having 5 to 30 aromatic ring atoms, in which one or more H atoms may be replaced by D, F, Cl, Br, I or CN;

the following compounds are excluded from the invention:

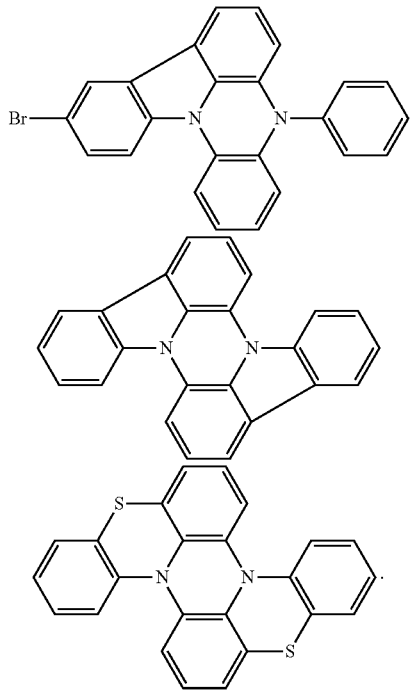

Adjacent radicals R are taken to mean radicals R which are bonded to carbon atoms which are linked directly to one another.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from O and/or S and optionally additionally N. An aryl group or heteroaryl group here is taken to mean either a simple aromatic ring, i.e. benzene, or a simple heteroaromatic ring, for example thiophene, furan, etc., or a condensed (fused) aryl or heteroaryl group, for example naphthalene, anthracene, phenanthrene, benzofuran, benzothiophene, etc. Aromatic rings linked to one another by a single bond, such as, for example, biphenyl, are, by contrast, not referred to as an aryl or heteroaryl group, but instead as an aromatic ring system.

Sulfur-containing or oxygen-containing heteroaryl groups in the sense of the present invention are heteroaryl groups which contain at least one sulfur atom or oxygen atom, in particular furan, thiophene, benzofuran, benzothiophene, dibenzofuran and dibenzothiophene.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from O and/or S and optionally additionally N. The heteroaryl groups present in the heteroaromatic ring system are exclusively sulfur-containing or oxygen-containing groups. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by one or more C atoms. Thus, for example, systems such as fluorene, 9,9'-spirobifluorene, 9,9-diarylfluorene, etc., are also intended to be taken to be aromatic ring systems in the sense of this invention, as are systems in which two or more aryl groups are connected, for example, by a short alkyl group. Furthermore, aromatic rings linked to one another by a single bond, such as, for example, biphenyl, are referred to as an aromatic ring system in the sense of this application.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethyihexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-80 aromatic ring atoms, which may also in each case be substituted by the above-mentioned radicals $R^2$ or $R^3$ and which may be linked via any desired positions on the aromatic or heteroaromatic group, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, phenothiazine, phenoxazine, oxazole, benzoxazole, naphthoxazole, anthroxazole, phenanthroxazole, isoxazole, 1,2-thiazole, 1,3-thiazole, benzothiazole, phenothiazine, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole and benzothiadiazole or groups derived from combination of these systems.

In a preferred embodiment of the invention, V stands for N.

In a further preferred embodiment of the invention, Y, $Y^1$, $Y^2$ and $Y^3$ stands, identically or differently on each occurrence, for a single bond, $C(R^1)_2$, $NR^1$, O or S, particularly preferably for a single bond or $C(R^1)_2$.

In a further preferred embodiment of the invention, a maximum of one of the groups X and Z per ring stands for N and the other groups X and Z in this ring stand for CR, or Z stands for C if a group $Y^1$ or $Y^2$ or $Y^3$ is bonded to this Z and X stands for C if a group L is bonded thereto. Particularly preferably, all X and Z stand for CR, or Z stands for C if a group $Y^1$ or $Y^2$ or $Y^3$ is bonded to this Z and X stands for C if a group L is bonded to this X.

A preferred embodiment of the formula (1) or (2) is thus a compound of the following formula (1a) or (2a),

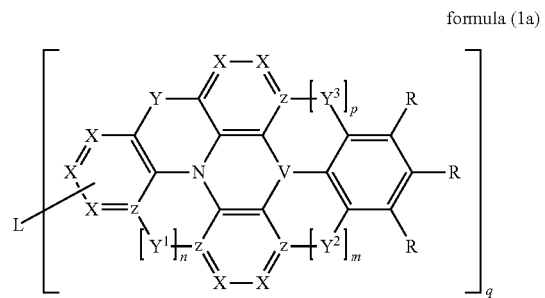

formula (1a)

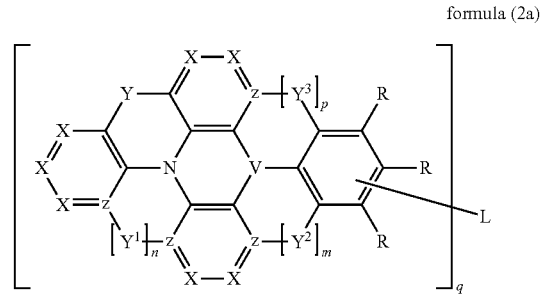

formula (2a)

where the following applies to the symbols used:

Y, $Y^1$, $Y^2$, $Y^3$ is, identically or differently on each occurrence, a single bond, $C(R^1)_2$, $NR^1$, O or S;

X, Z is CR or N, with the proviso that a maximum of one of the groups X and Z per ring stands for N and the other groups X and Z in this ring stand for CR, or Z stands for C if a group $Y^1$ or $Y^2$ or $Y^3$ is bonded to this Z and X stands for C if a group L is bonded to this X;

and the other symbols and indices used have the meanings given above.

A particularly preferred embodiment of the formula (1) or (2) is a compound of the following formula (1 b) or (2b), formula (1b)

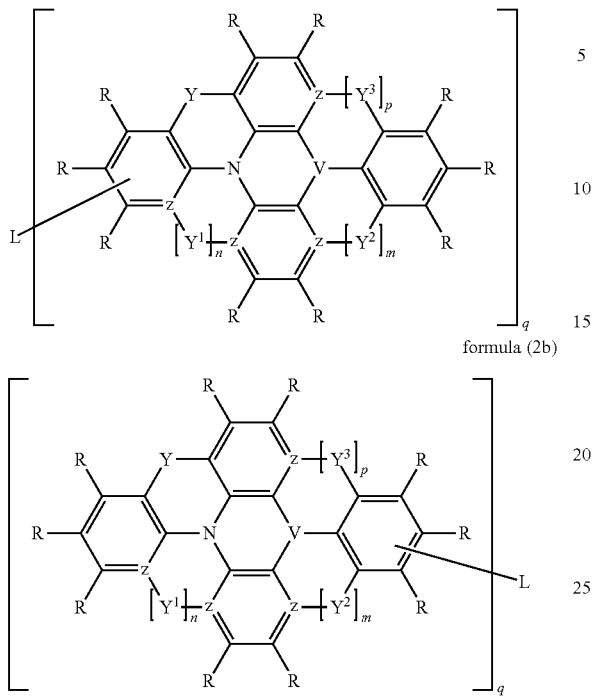

formula (2b)

where the following applies to the symbols used:
Y, $Y^1$, $Y^2$, $Y^3$ is, identically or differently on each occurrence, a single bond, $C(R^1)_2$, $NR^1$, O or S, in particular a single bond or $C(R^1)_2$;
Z is CR, or Z is C if a group $Y^1$ or $Y^2$ or $Y^3$ is bonded to this Z;
and the other symbols and indices used have the meanings given above;
the radical R is not present here if a group L is bonded in this position.

Preference is furthermore given to compounds of the formula (1), (1a), (1b) or (2), (2a), (2b) in which Y stands for a single bond. Preference is likewise given to compounds of the formula (1) or (2) in which Y stands for $C(R^1)_2$, $NR^1$, O or S and $Y^2$ stands, identically or differently, for $C(R^1)_2$, $NR^1$, O or S and n=0 and p=0. Preference is likewise given to compounds of the formula (1) or (2) in which Y stands for $C(R^1)_2$, $NR^1$, O or S and $Y^3$ stands, identically or differently, for $C(R^1)_2$, $NR^1$, O or S and n=0 and m=0.

Preferred embodiments of the formula (1) or (1a) or (1b) are thus the compounds of the following formulae (3) to (5) and preferred embodiments of the formula (2) or (2a) or (2b) are the compounds of the following formulae (6) to (8), formula (3)

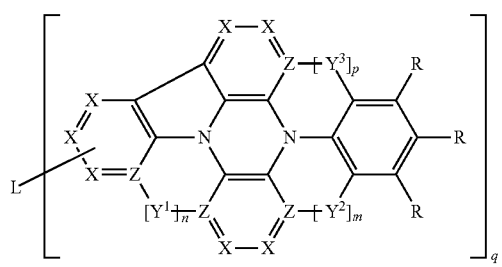

formula (4)

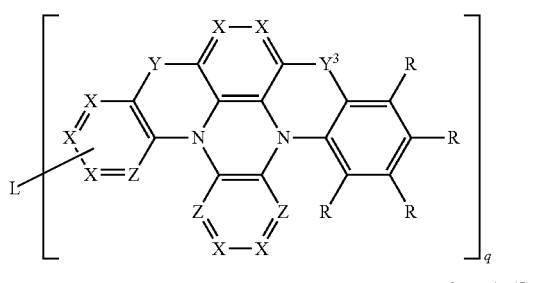

formula (5)

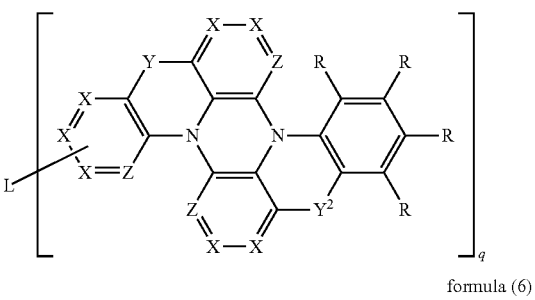

formula (6)

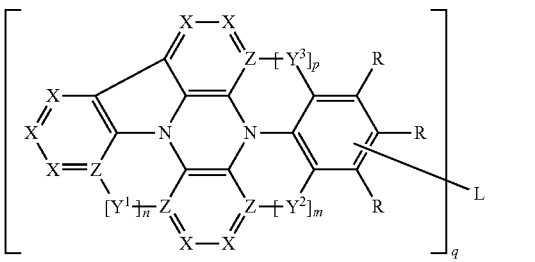

formula (7)

formula (8)

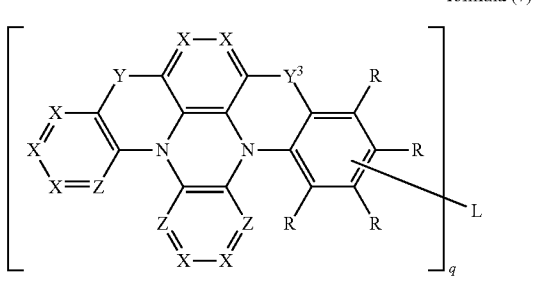

where the symbols and indices used have the meanings given above and the group R is not present if a group L is bonded in this position.

In a preferred embodiment of the compounds of the formula (1) or formula (2) or the preferred embodiments mentioned above, the index q=1 and L stands for a group R.

Preferred embodiments of the compounds of the formulae (3) to (8) are thus the compounds of the following formulae (3a), (4a) and (5a), formula (3a)
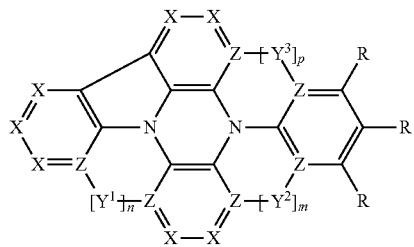

formula (4a)
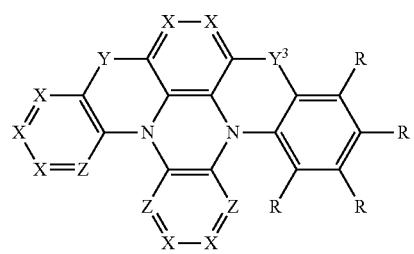

formula (5a)
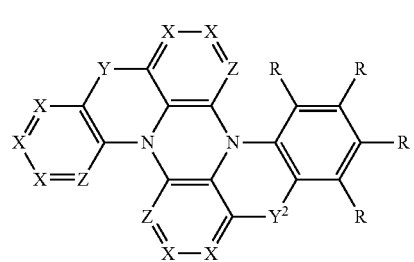

where the symbols and indices used have the meanings given above.

Preferred embodiments of the compound of the formula (3) are the compounds of the following formulae (9) to (13), and preferred embodiments of the compound of the formula (6) are the compounds of the following formulae (14) to (18), formula (9)
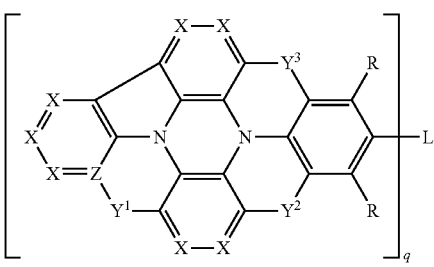

formula (10)
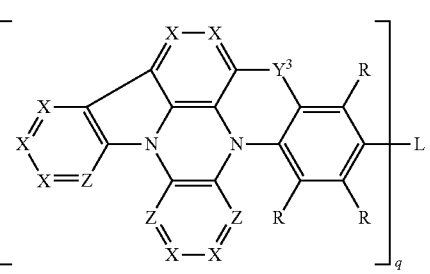

formula (11)
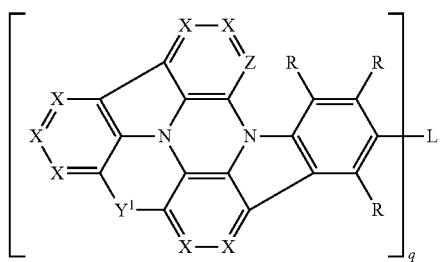

formula (12)
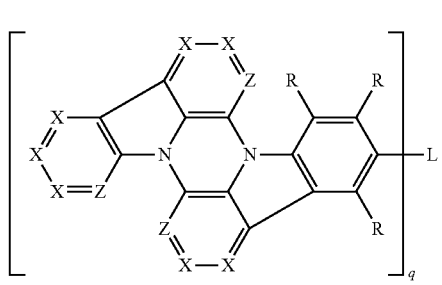

formula (13)
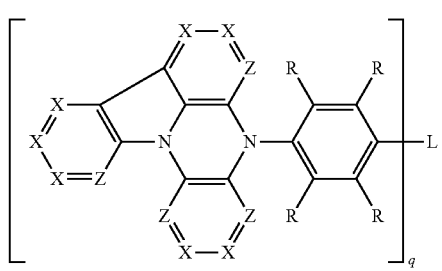

formula (14)
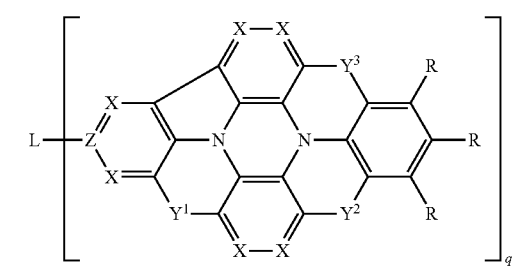

formula (15)
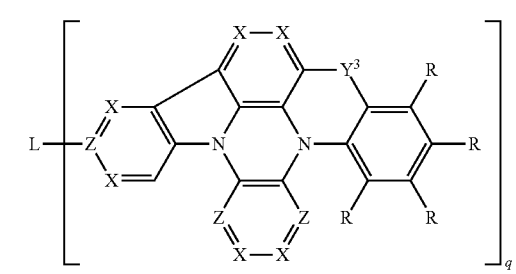

-continued formula (16)

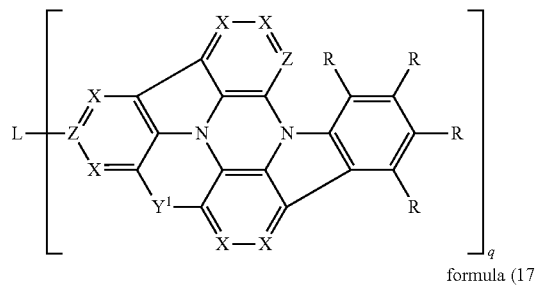

formula (17)

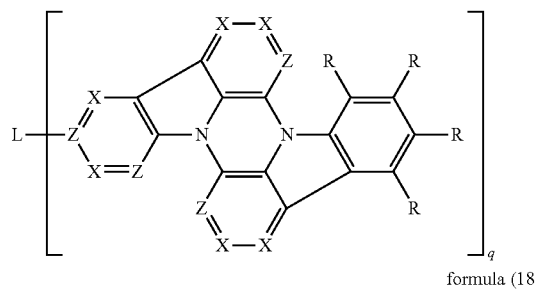

formula (18)

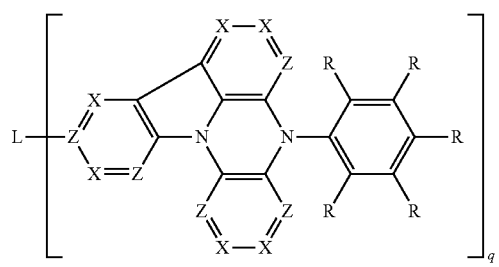

where the symbols and indices used have the meanings given above. In formula (9), (10), (14) and (15), $Y^3$ preferably stands for a single bond.

Preferred embodiments of the compound of the formula (3a) are the compounds of the following formulae (19) to (23), formula (19)

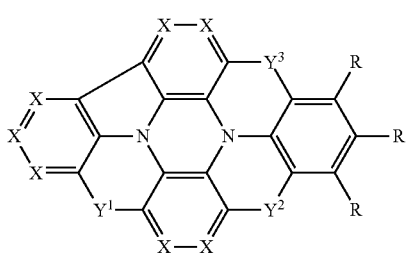

formula (20)

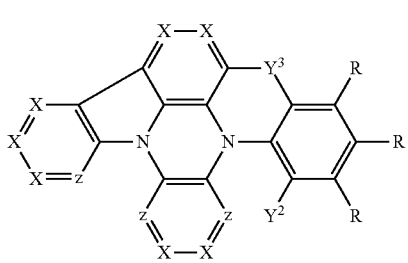

-continued formula (21)

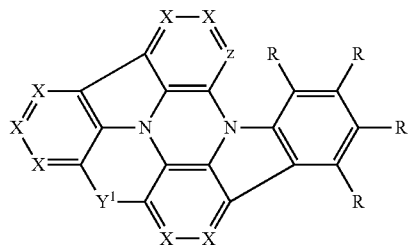

formula (22)

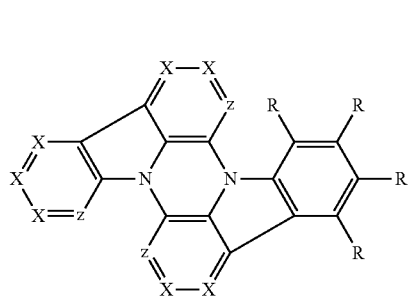

formula (23)

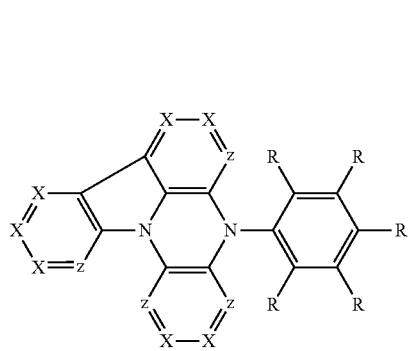

where the symbols and indices used have the meanings given above. In formula (19) and (20), $Y^3$ preferably stands for a single bond.

In a preferred embodiment of the invention, in total a maximum of one of the groups X and Z in the compounds of the formula (3) to (23) per ring stand for N. Particularly preferably, all groups X and Z stand for CR or C.

Particularly preferred embodiments of the invention are therefore the compounds of the following formulae (19a) to (23a), formula (19a)

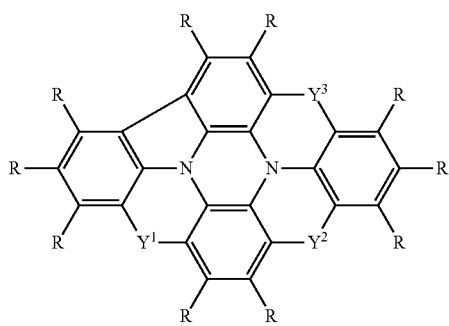

formula (20a)
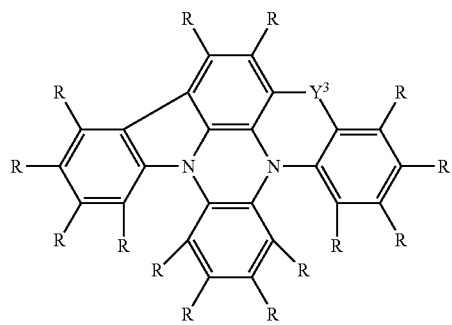
formula (21a)
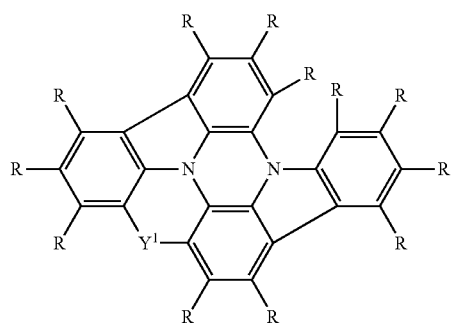
formula (22a)
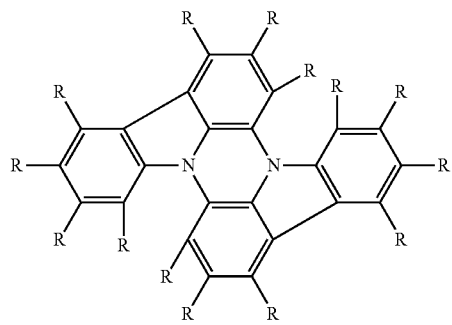
formula (23a)
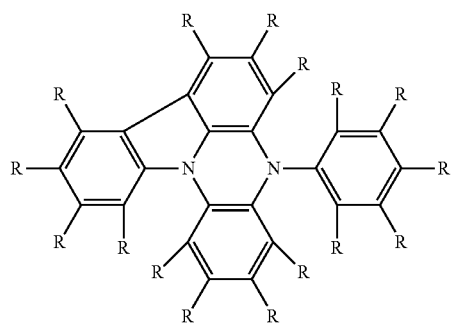
where the symbols and indices used have the meanings given above. In formula (19a) and (20a), Y³ preferably stands for a single bond.
Very particularly preferred embodiments of the invention are therefore the compounds of the following formulae (19b) to (23b),
formula (19b)
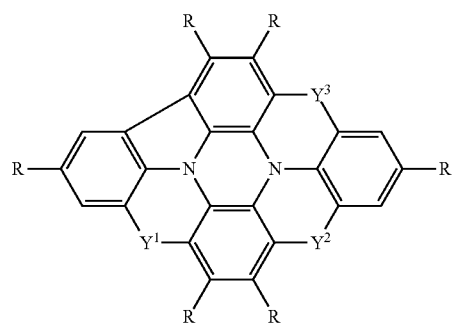
formula (20b)
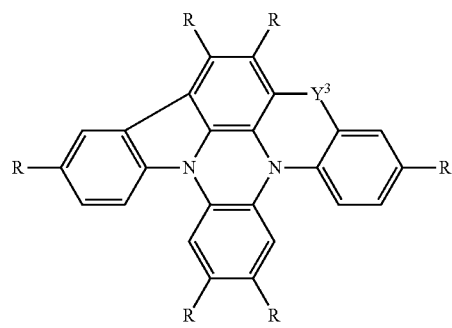
formula (21b)
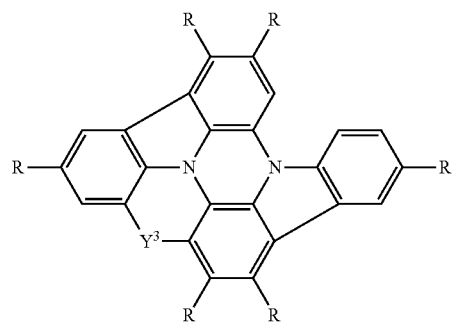
formula (22b)
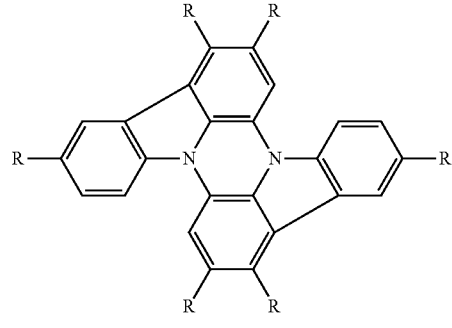

formula (23b)

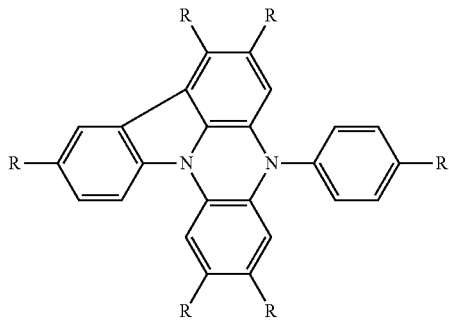

where the symbols and indices used have the meanings given above. In formula (19b) and (20b), $Y^3$ preferably stands for a single bond.

Preferred embodiments of the formulae (4a) and (5a) are the compounds of the following formulae (24) and (25), formula (24)

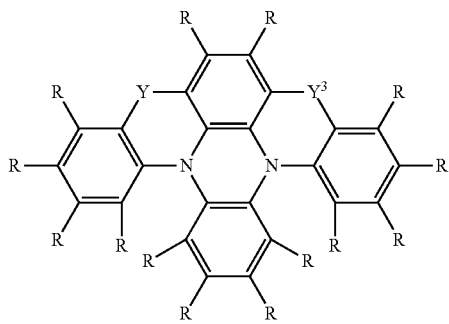

formula (25)

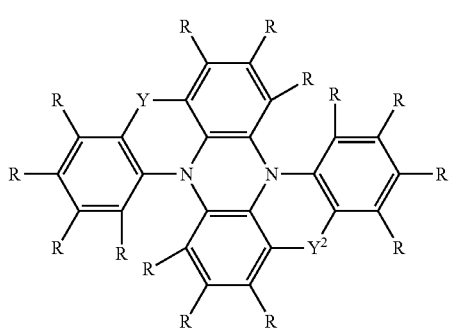

where the symbols used have the meanings given above and Y, $Y^2$ and $Y^3$ preferably stands, identically or differently on each occurrence, for a single bond, $C(R^1)_2$, $NR^1$, O or S, in particular, identically or differently, for a single bond or $C(R^1)_2$.

Preferred embodiments of the formulae (24) and (25) are the compounds of the following formulae (24a) and (25a), formula (24a)

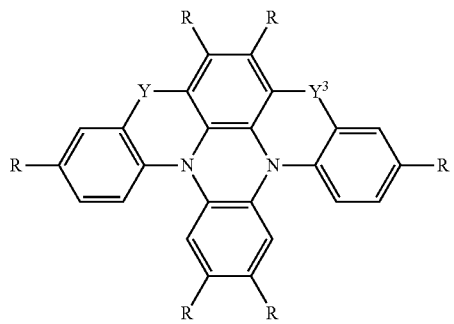

formula (25a)

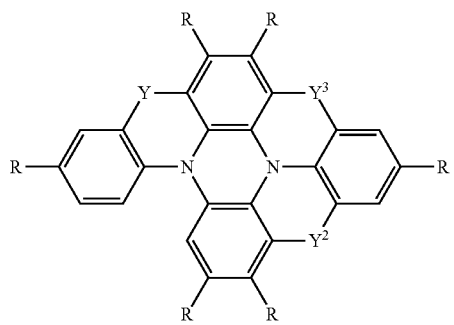

where the symbols used have the meanings given above and Y, $Y^2$ and $Y^3$ preferably stands, identically or differently on each occurrence, for a single bond, $C(R^1)_2$, $NR^1$, O or S, in particular, identically or differently, for a single bond or $C(R^1)_2$.

Preferred substituents R are selected, identically or differently on each occurrence, from the group consisting of H, D, F, CN, C(=O)Ar, C(=O)$R^2$, P(=O)(Ar)$_2$, a straight-chain alkyl group having 1 to 10 C atoms or a branched or cyclic alkyl group having 3 to 10 C atoms, each of which may be substituted by one or more radicals $R^2$, where one or more non-adjacent CH$_2$ groups may be replaced by O or S and where one or more H atoms may be replaced by D or F, an aromatic ring system having 6 to 24 aromatic ring atoms, which may be substituted by one or more radicals $R^2$, a heteroaromatic ring system having 5 to 24 aromatic ring atoms, which contains, as heteroaryl groups, exclusively sulfur-containing or oxygen-containing heteroaryl groups and which may be substituted by one or more radicals $R^2$, or an aralkyl or heteroalkyl group having 5 to 24 aromatic ring atoms, which may be substituted by one or more radicals $R^2$, where two adjacent substituents R may optionally form a condensed-on benzo ring with one another, which may be substituted by one or more radicals $R^2$.

Particularly preferred substituents R are selected, identically or differently on each occurrence, from the group consisting of H, a straight-chain alkyl group having 1 to 4 C atoms, in particular methyl, or a branched or cyclic alkyl group having 3 to 8 C atoms, each of which may be substituted by one or more radicals $R^2$, an aromatic ring system having 6 to 24 aromatic ring atoms, which may be substituted by one or more radicals $R^2$, a heteroaromatic ring system having 5 to 24 aromatic ring atoms, which contains, as heteroaryl groups, exclusively sulfur-containing or oxygen-containing heteroaryl groups and which may be substituted by one or more radicals $R^2$.

If R stands for an aromatic or heteroaromatic ring system, this is then preferably selected from the groups of the following formulae (26) to (58),
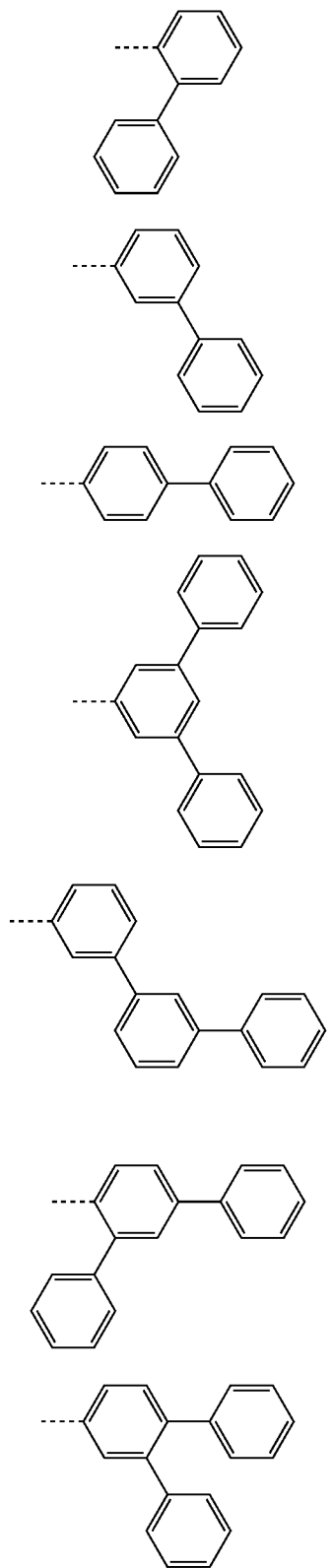
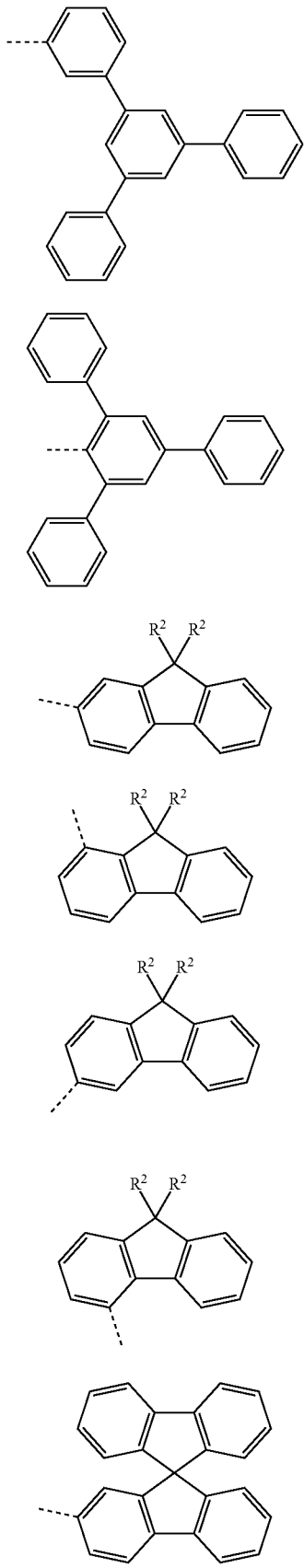

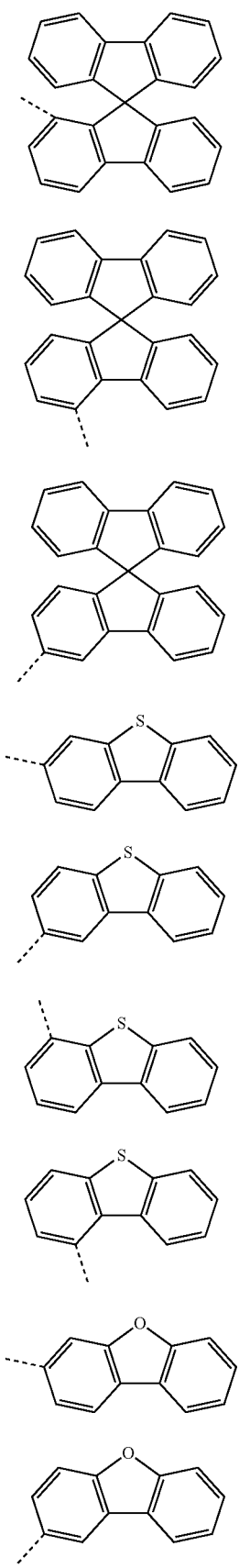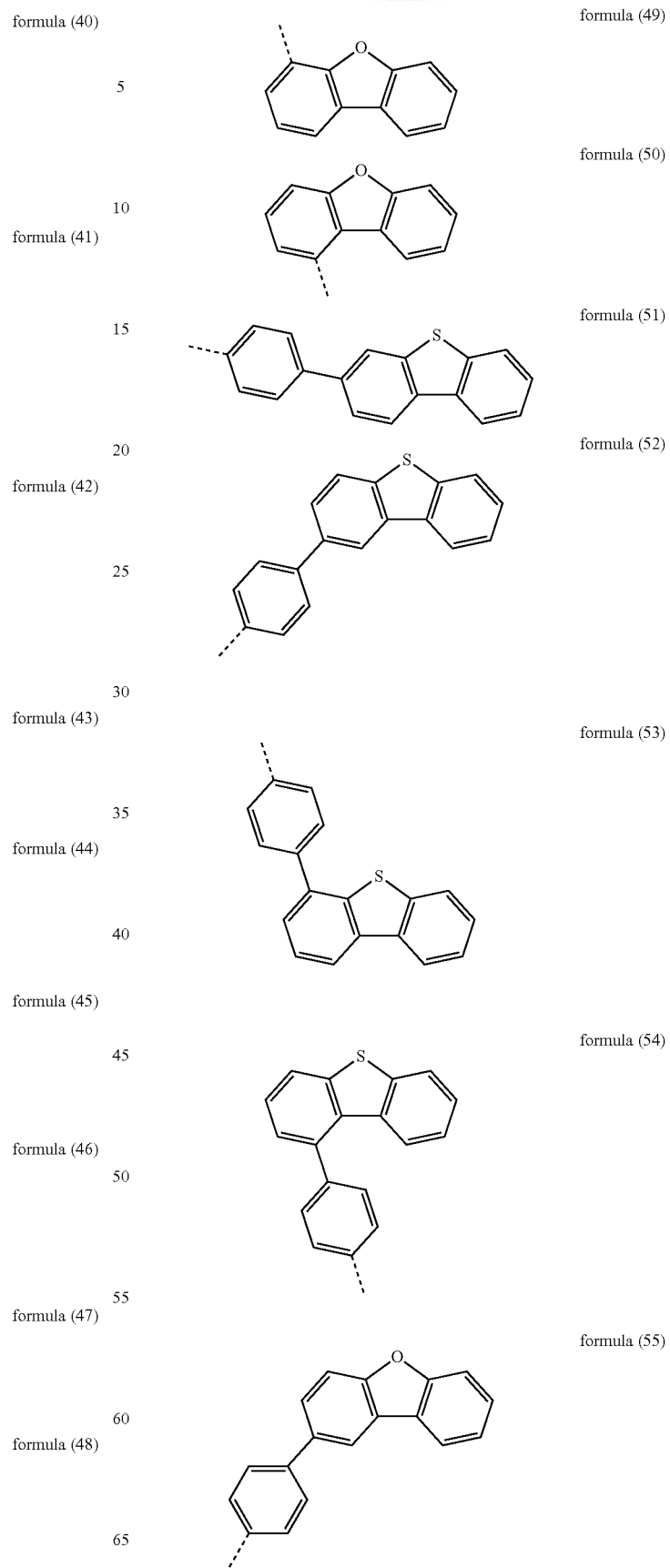

formula (56)

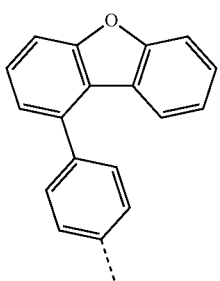

formula (57)

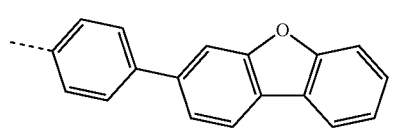

formula (58)

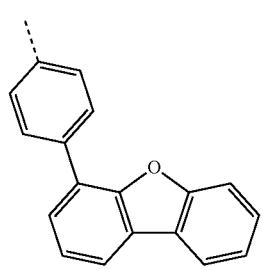

where the dashed bond indicates the bonding to the basic structure and the groups may be substituted by one or more radicals $R^2$, but are preferably unsubstituted.

$R^2$ in the groups of the formulae (35) to (38) preferably stands, identically or differently, for an alkyl group having 1 to 10 C atoms, in particular for methyl, or a phenyl group, which may be substituted by one or more radicals $R^3$.

Preferred substituted embodiments of the formula (28) are the following formulae (28a) and (28b), preferred embodiments of the formula (31) is the formula (31a), preferred embodiments of the formula (35) are the following formulae (35a), (35b), (35c) and (35d), preferred embodiments of the formula (36) are the following formulae (36a), (36b), (36c) and (36d), preferred embodiments of the formula (37) are the following formulae (37a), (37b), (37c) and (37d), and preferred embodiments of the formula (38) are the following formulae (38a), (38b), (38c) and (38d), formula (28a)

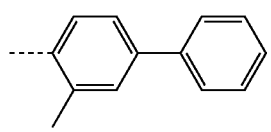

formula (28b)

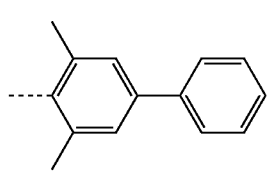

formula (31a)

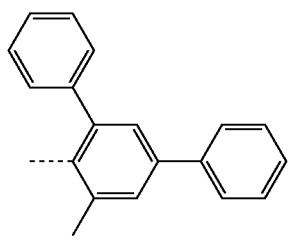

formula (35a)

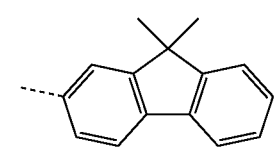

formula (35b)

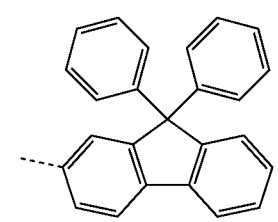

formula (35c)

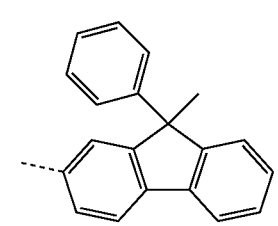

formula (35d)

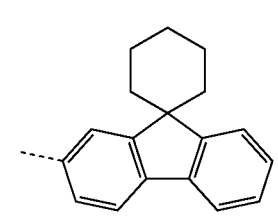

formula (36a)

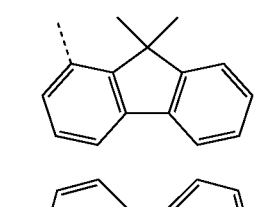

formula (36b)

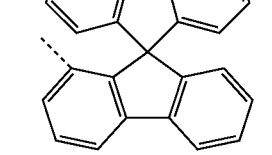

formula (36c)

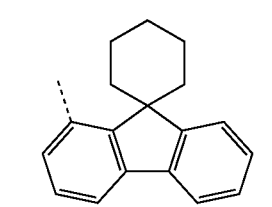

-continued formula (36c)

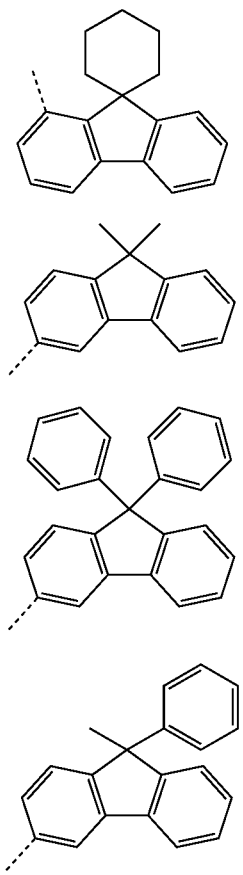

formula (37a)

formula (37b)

formula (37c)

formula (37d)

formula (38a)

formula (38b)

-continued formula (38c)

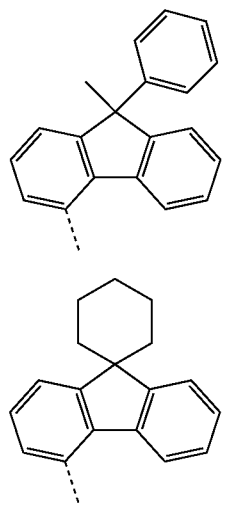

formula (38d)

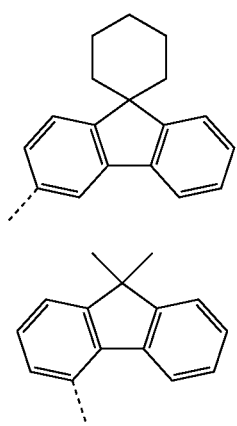

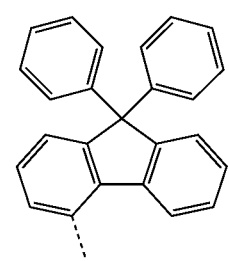

where the dashed bond indicates the bonding to the basic structure.

If Y or $Y^1$ or $Y^2$ or $Y^3$ stands for $C(R^1)_2$, $R^1$ is preferably selected on each occurrence, identically or differently, from the group consisting of H, D, F, a straight-chain alkyl group having 1 to 10 C atoms or a branched or cyclic alkyl group having 3 to 10 C atoms, each of which may be substituted by one or more radicals $R^2$, where one or more non-adjacent $CH_2$ groups may be replaced O or S and where one or more H atoms may be replaced by D or F, an aromatic ring system having 5 to 24 aromatic ring atoms, which may be substituted by one or more radicals $R^2$, a heteroaromatic ring system having 5 to 24 aromatic ring atoms, which contains, as heteroaryl groups, exclusively sulfur-containing or oxygen-containing heteroaryl groups and which may be substituted by one or more radicals $R^2$, or an aralkyl or heteroaralkyl group having 5 to 24 aromatic ring atoms, which may be substituted by one or more radicals $R^2$, where the substituents $R^1$ which are bonded to the same carbon atom may optionally form a mono- or polycyclic, aliphatic, aromatic or heteroaromatic ring system with one another and may thus form a Spiro system, which may be substituted by one or more radicals $R^2$. $R^1$ is particularly preferably selected on each occurrence, identically or differently, from the group consisting of a straight-chain alkyl group having 1 to 4 C atoms, in particular methyl, or a branched alkyl group having 3 to 10 C atoms, each of which may be substituted by one or more radicals $R^2$, or a phenyl or ortho-, meta- or para-biphenyl group, which may be substituted by one or more radicals $R^2$, where the substituents $R^1$ which are bonded to the same carbon atom may optionally form a mono- or polycyclic, aliphatic, aromatic or heteroaromatic ring system with one another and may thus form a Spiro system, which may be substituted by one or more radicals $R^2$.

If Y or $Y^1$ or $Y^2$ or $Y^3$ stands for $N(R^1)$, $R^1$ is preferably selected on each occurrence, identically or differently, from the group consisting of a straight-chain alkyl group having 1 to 10 C atoms or a branched or cyclic alkyl group having 3 to 10 C atoms, each of which may be substituted by one or more radicals $R^2$, where one or more non-adjacent $CH_2$ groups which are not bonded directly to the nitrogen may be replaced O or S and where one or more H atoms may be replaced by D or F, an aromatic ring system having 5 to 24 aromatic ring atoms, which may be substituted by one or more radicals R², a heteroaromatic ring system having 5 to 24 aromatic ring atoms, which contains, as heteroaryl groups, exclusively sulfur-containing or oxygen-containing heteroaryl groups and which may be substituted by one or more radicals R², or an aralkyl or heteroaralkyl group having 5 to 24 aromatic ring atoms, which may be substituted by one or more radicals R². R¹ is particularly preferably selected on each occurrence, identically or differently, from the group consisting of an aromatic ring system having 5 to 24 aromatic ring atoms, which may be substituted by one or more radicals R², or a heteroaromatic ring system having 5 to 24 aromatic ring atoms, which contains, as heteroaryl groups, exclusively sulfur-containing or oxygen-containing heteroaryl groups and which may be substituted by one or more radicals R².

For compounds which are processed by vacuum evaporation, the alkyl groups in the radicals R and R¹ preferably have not more than four C atoms, particularly preferably not more than one C atom. For compounds which are processed from solution, compounds which are substituted by alkyl groups having up to 10 C atoms or which are substituted by oligoarylene groups, for example ortho-, meta-, para- or branched terphenyl groups or quaterphenyl groups or ortho-, meta- or para-biphenyl groups, are also particularly suitable.

In a further preferred embodiment of the invention, L is a divalent or polyvalent straight-chain alkylene or alkylidene group having 1 to 10 C atoms or a branched or cyclic alkylene or alkylidene group having 3 to 10 C atoms, which may be substituted by in each case one or more radicals R², where one or more H atoms may be replaced by D or F, or an at least divalent aromatic ring system having 5 to 24 aromatic ring atoms, which may be substituted by one or more radicals R², or an or heteroaromatic ring system having 5 to 24 aromatic ring atoms, which contains, as heteroaryl groups, exclusively sulfur-containing or oxygen-containing heteroaromatic groups and which may be substituted by one or more radicals R², or L is a chemical bond.

The above-mentioned embodiments of the invention can be combined with one another as desired. The embodiments of the invention mentioned above as preferred are particularly preferably combined with one another.

Examples of preferred compounds in accordance with the above-mentioned embodiments or compounds as can preferably be employed in electronic devices are the following compounds.

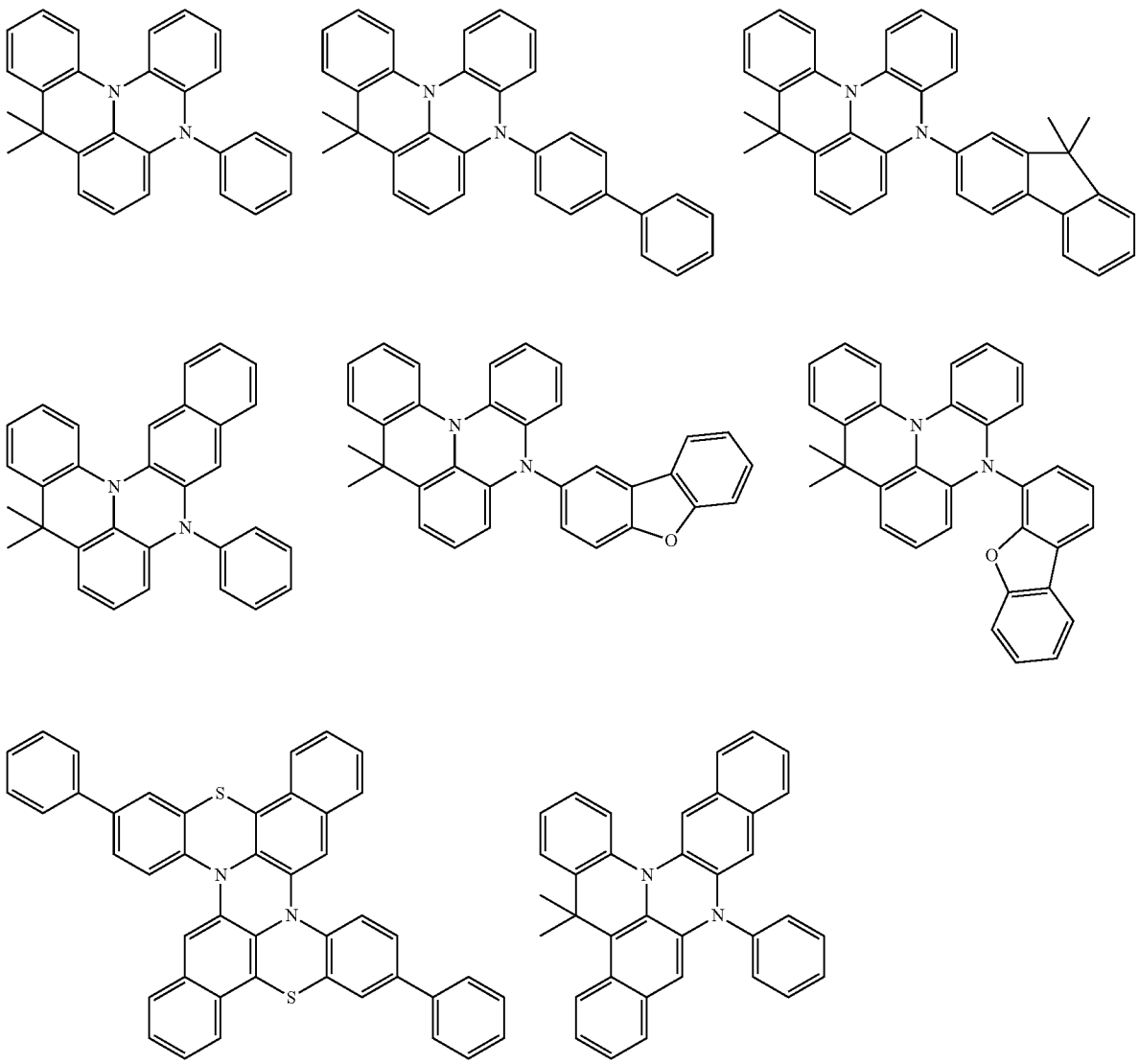

-continued
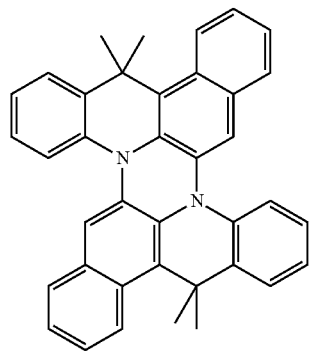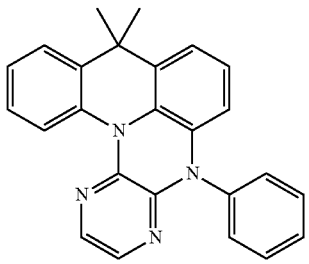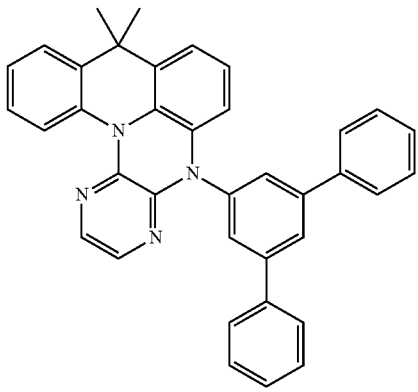
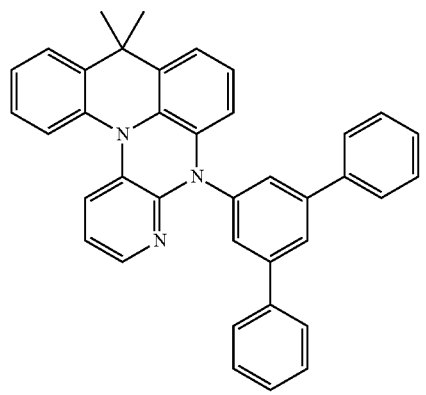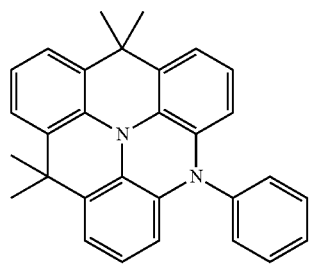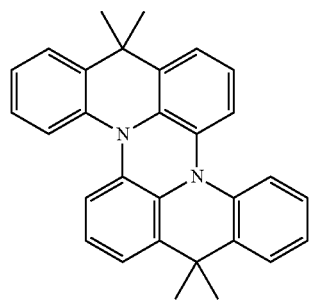
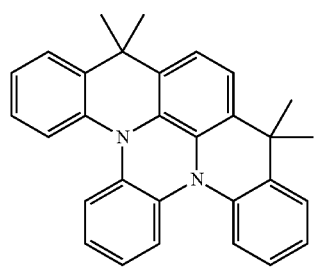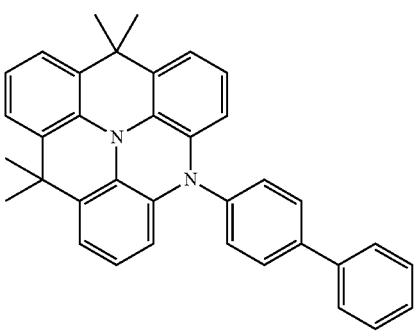
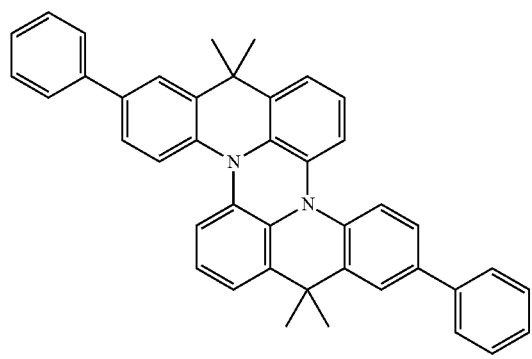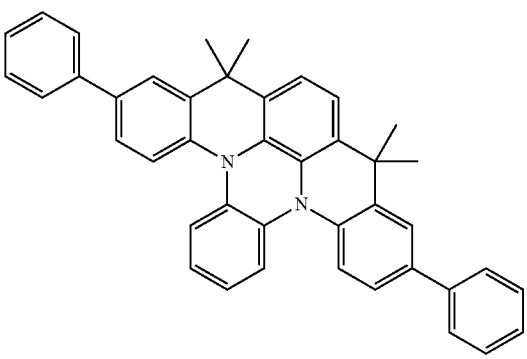

-continued
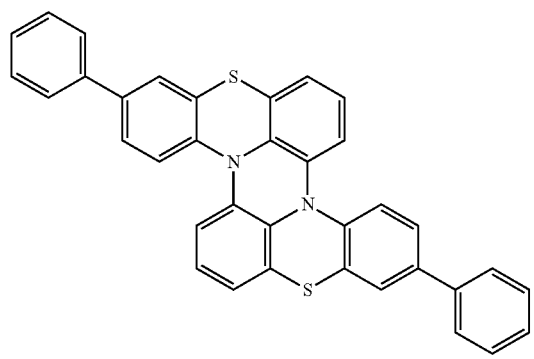
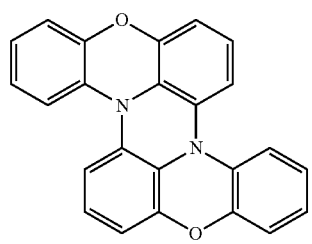
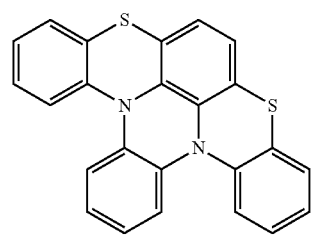
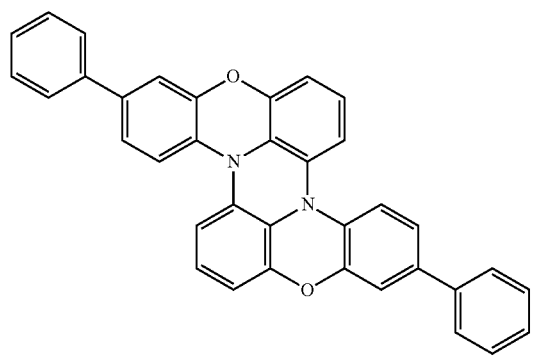
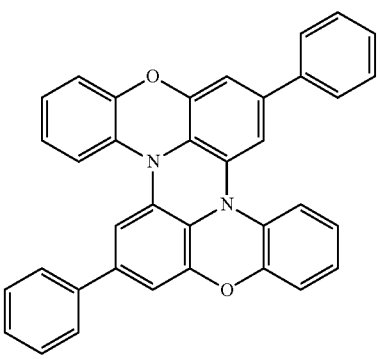
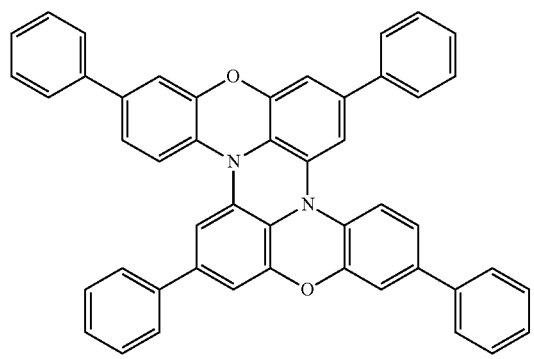
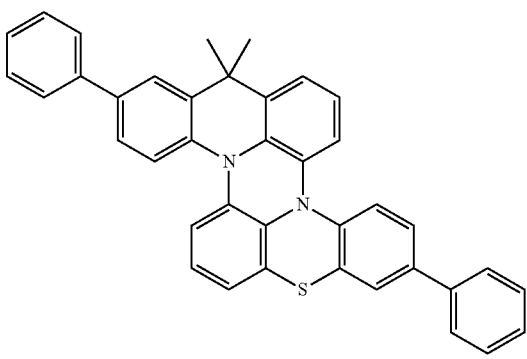
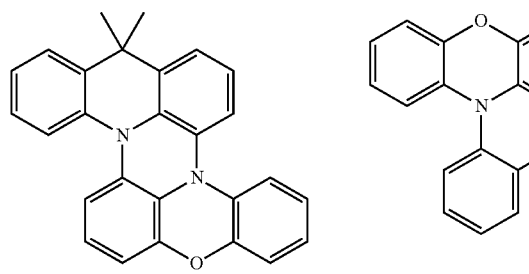
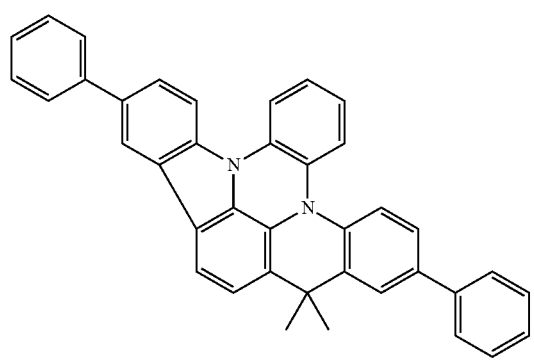
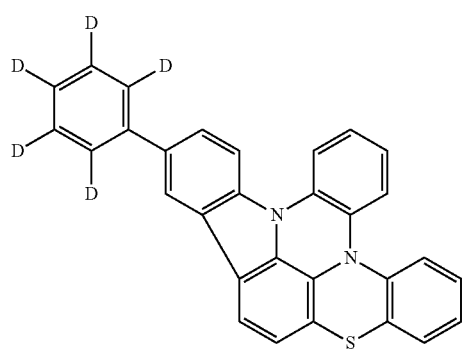

-continued
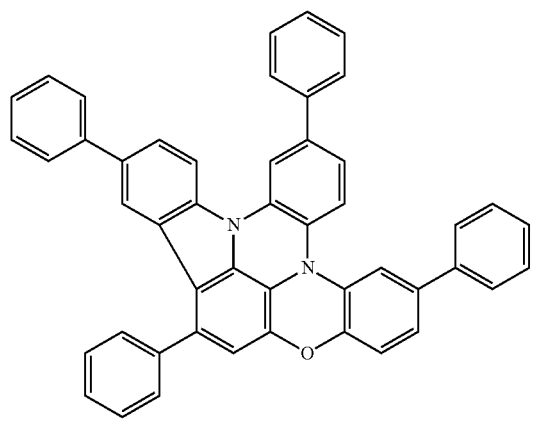
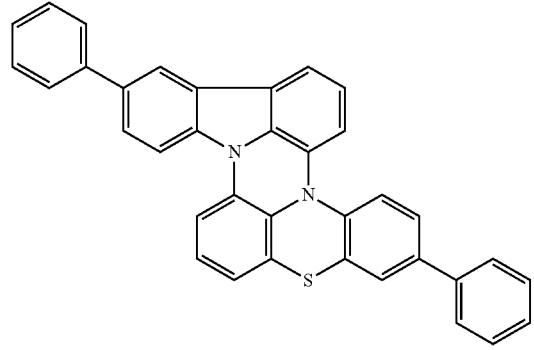
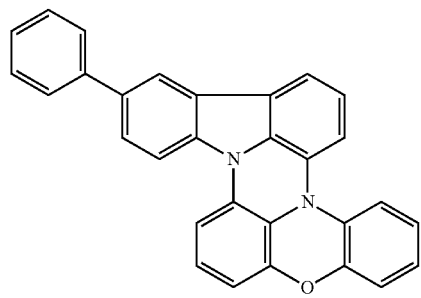
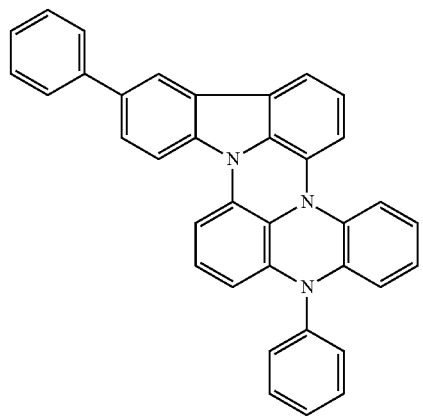
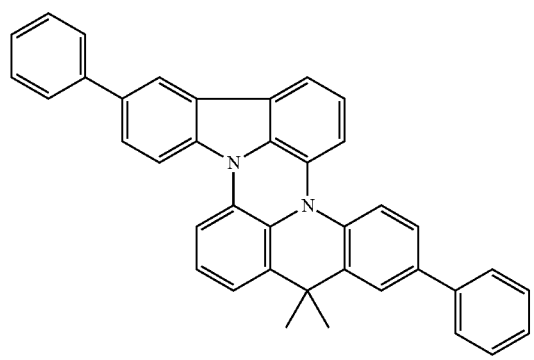
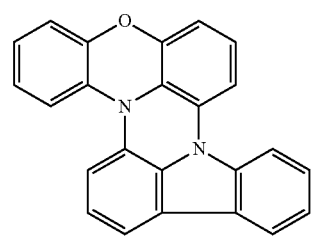
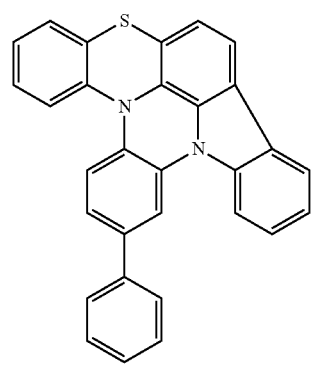
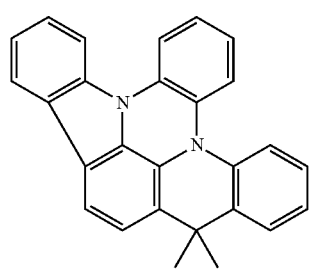
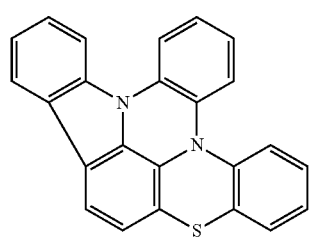
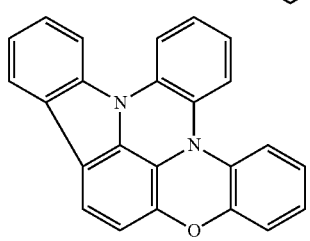
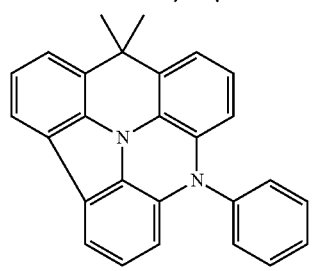
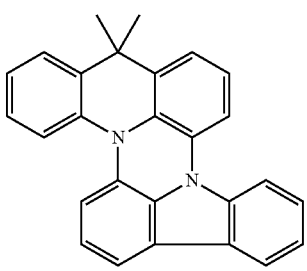
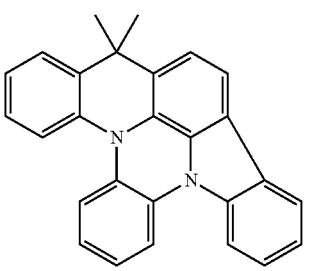

-continued
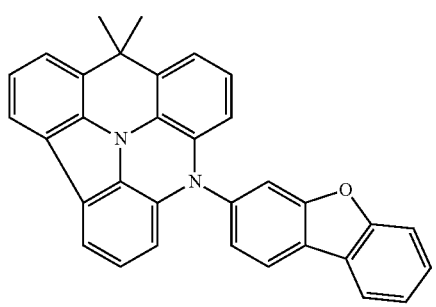
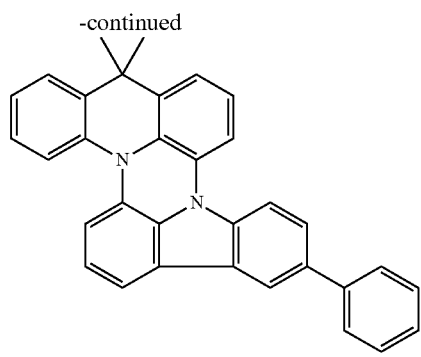
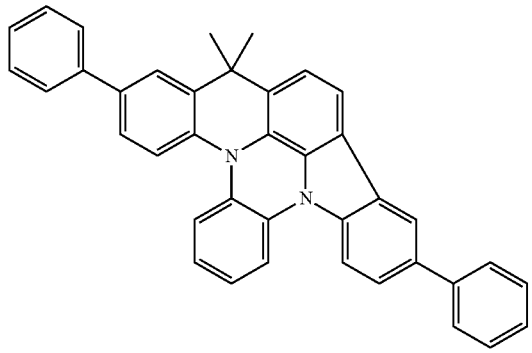
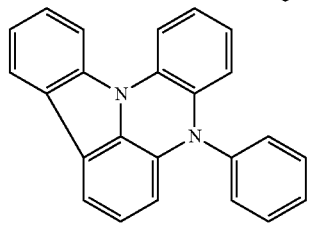
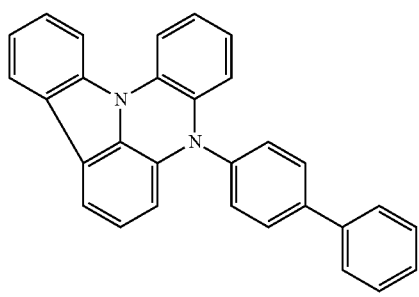
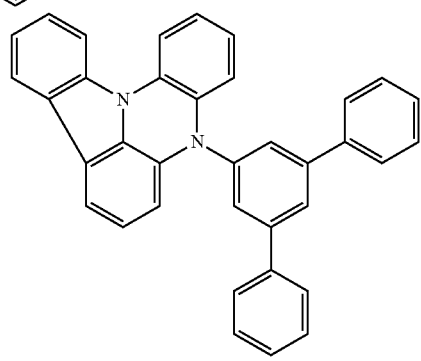
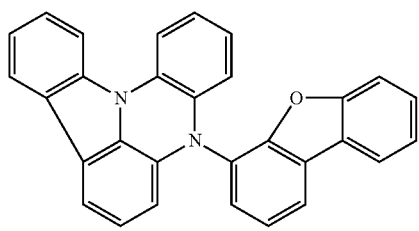
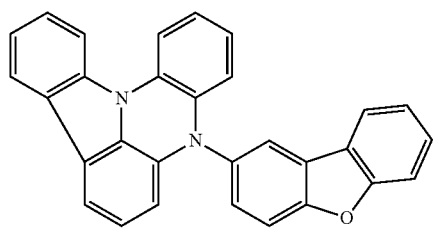
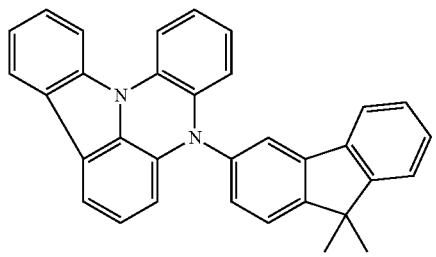
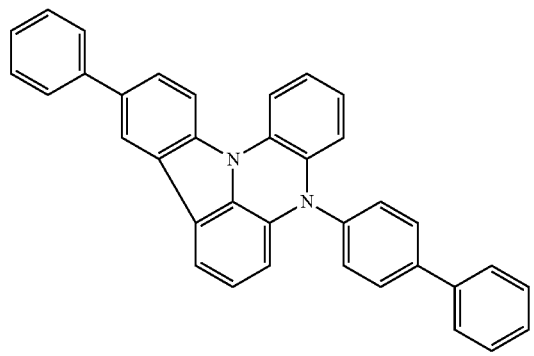

-continued
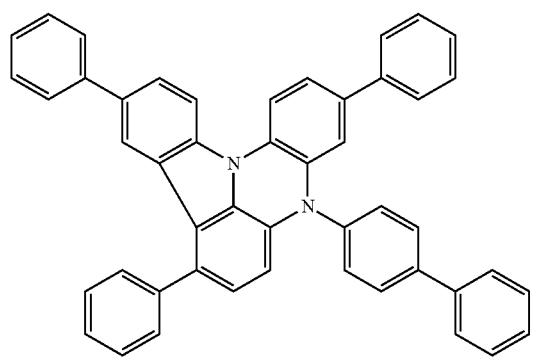
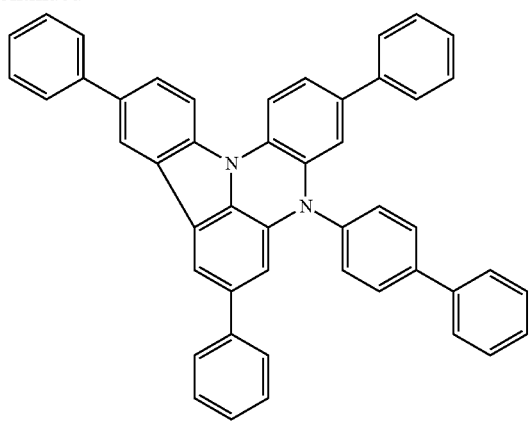
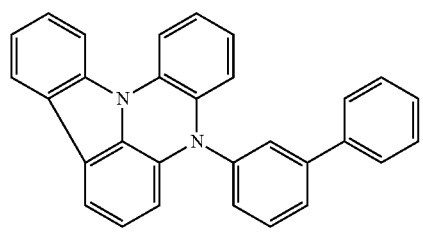
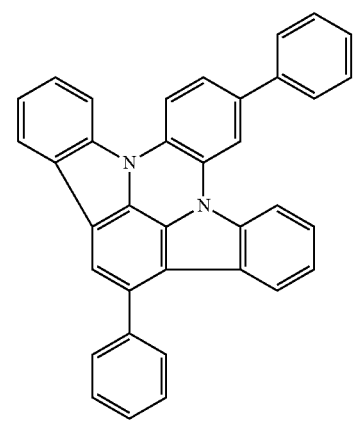
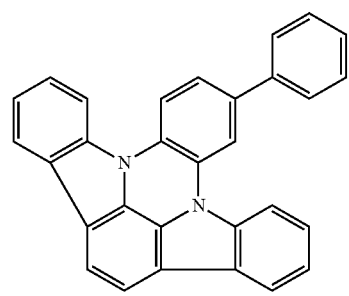
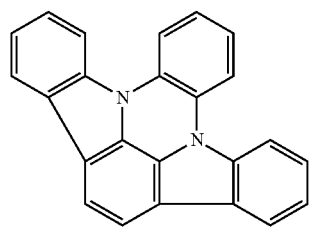
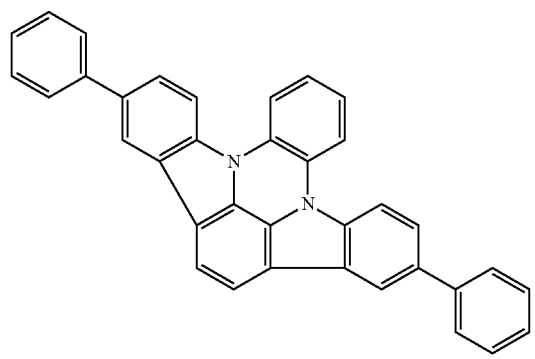
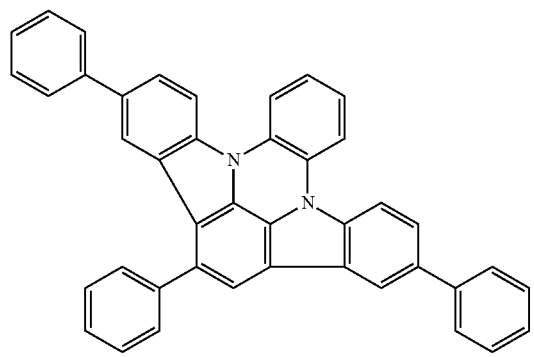
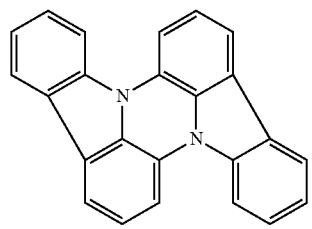

-continued
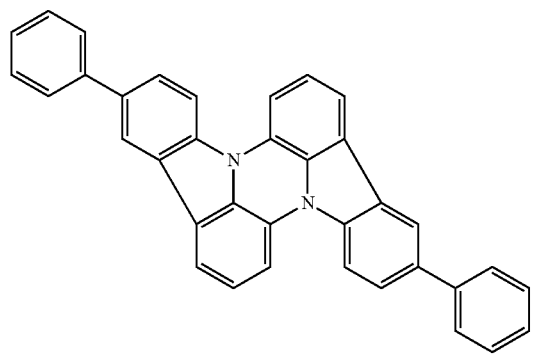
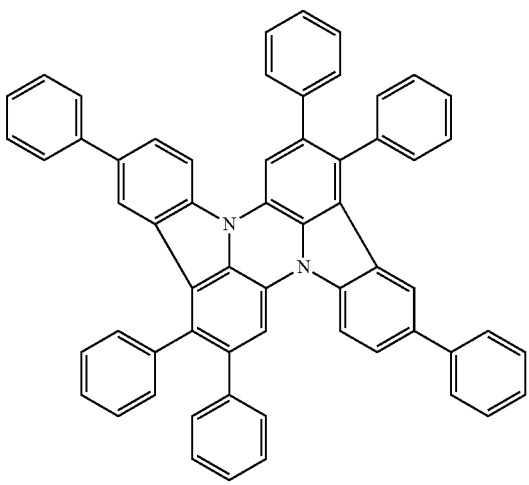
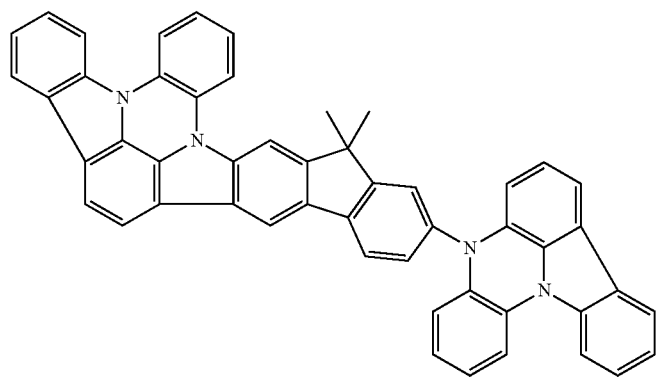
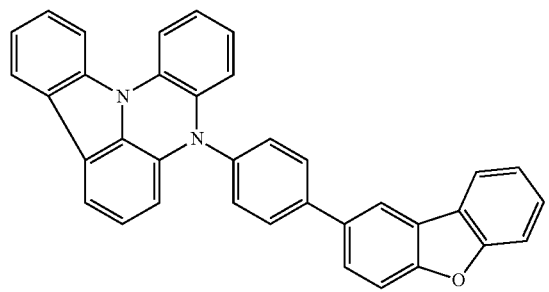
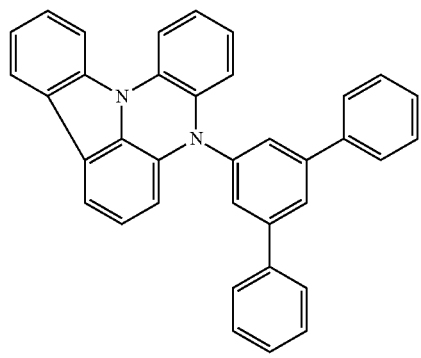
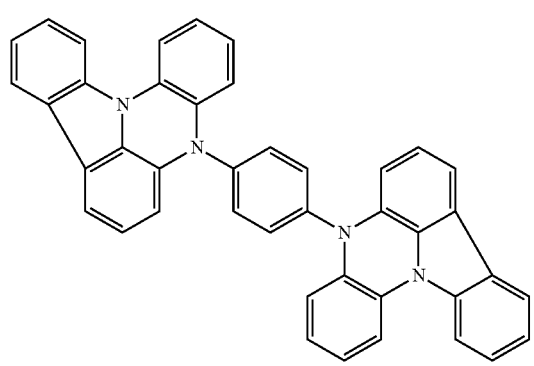
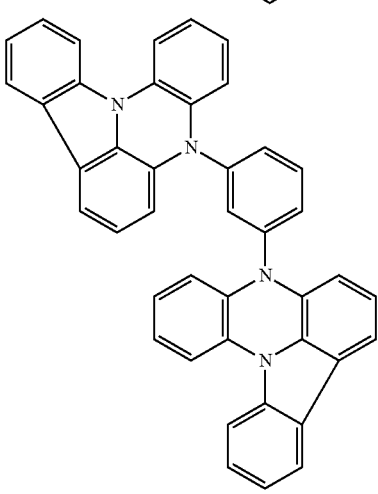

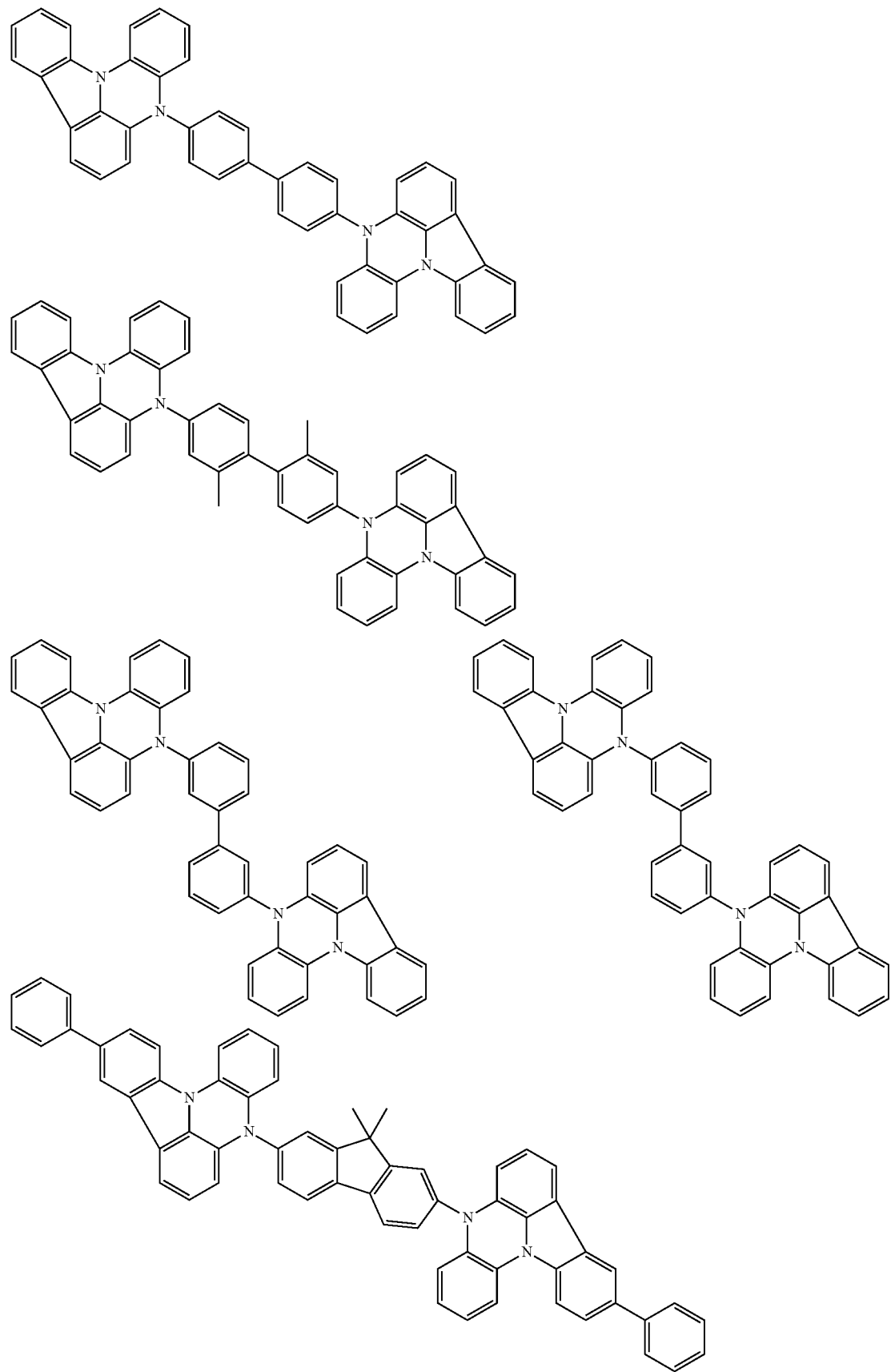

-continued
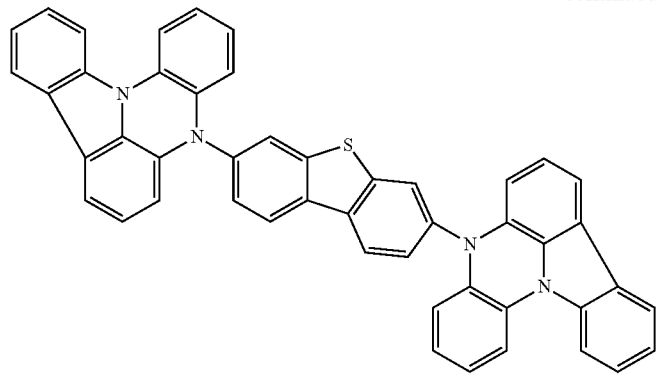
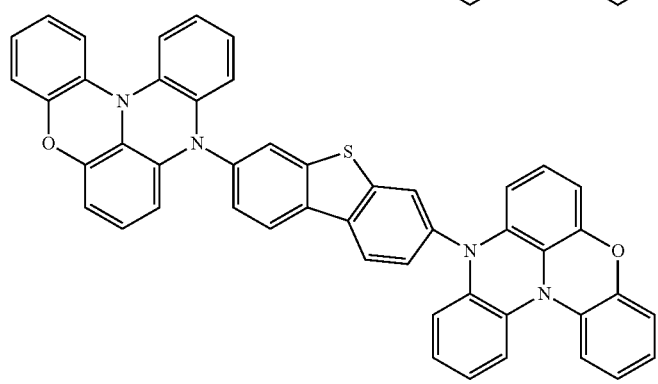
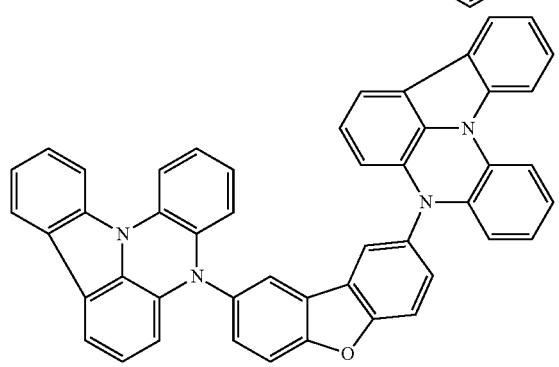
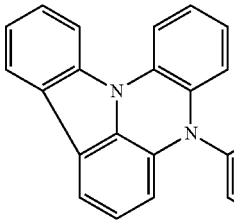
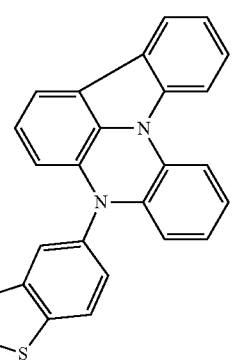
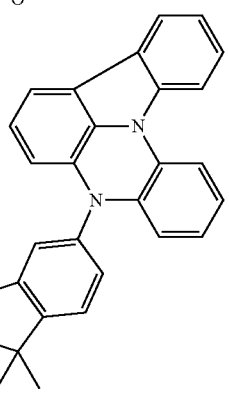
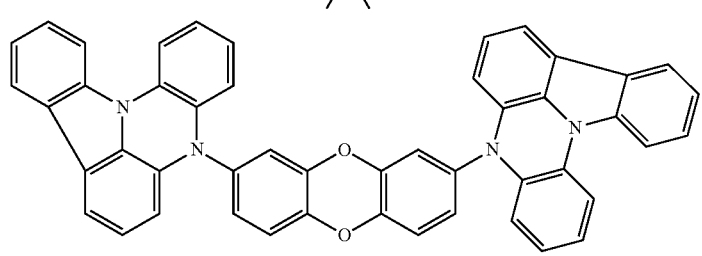

-continued
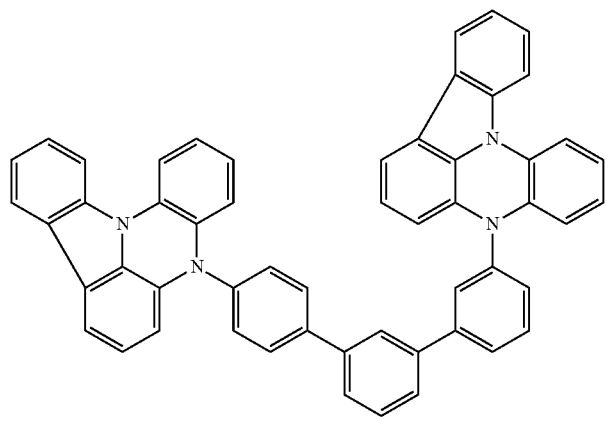
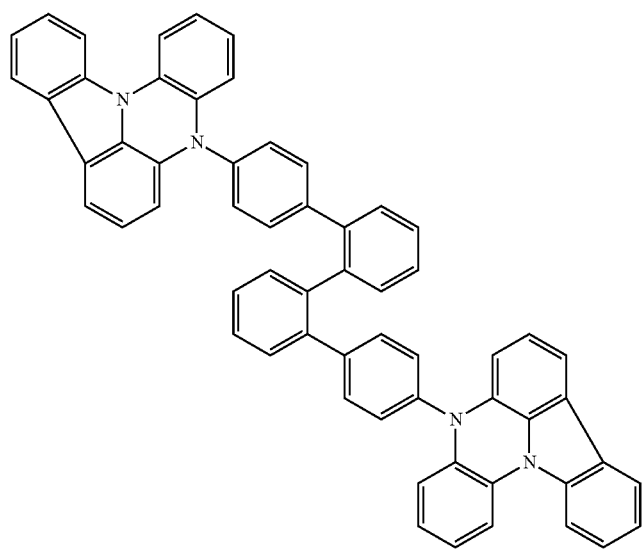
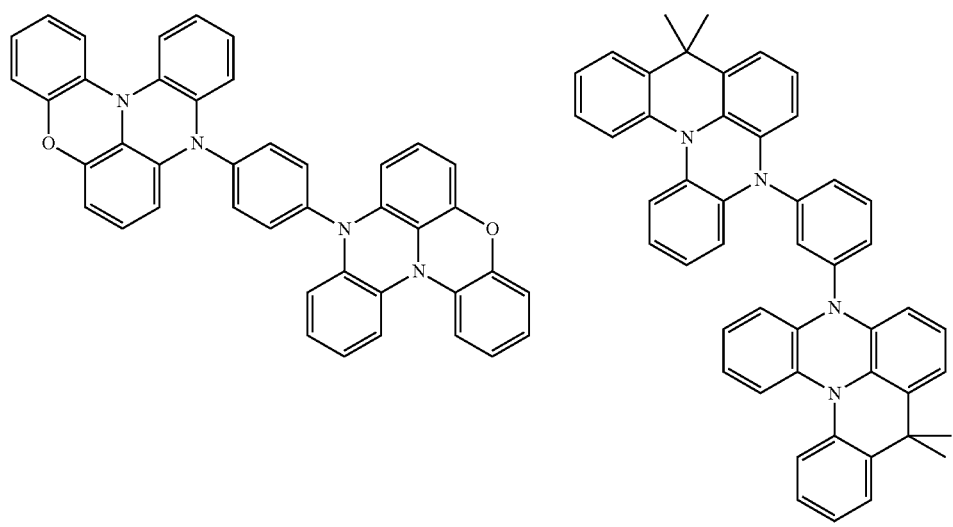

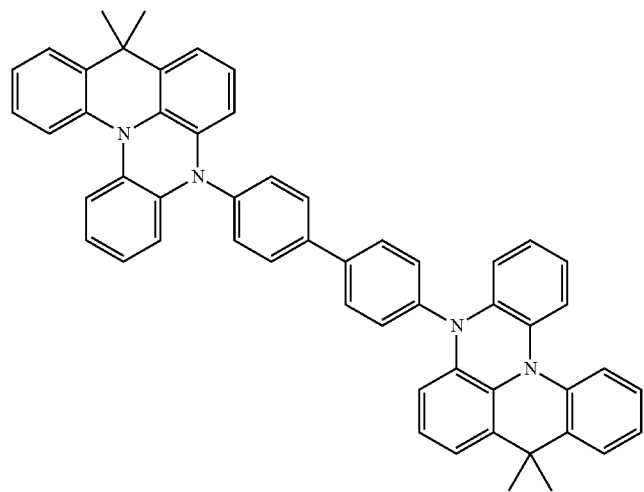
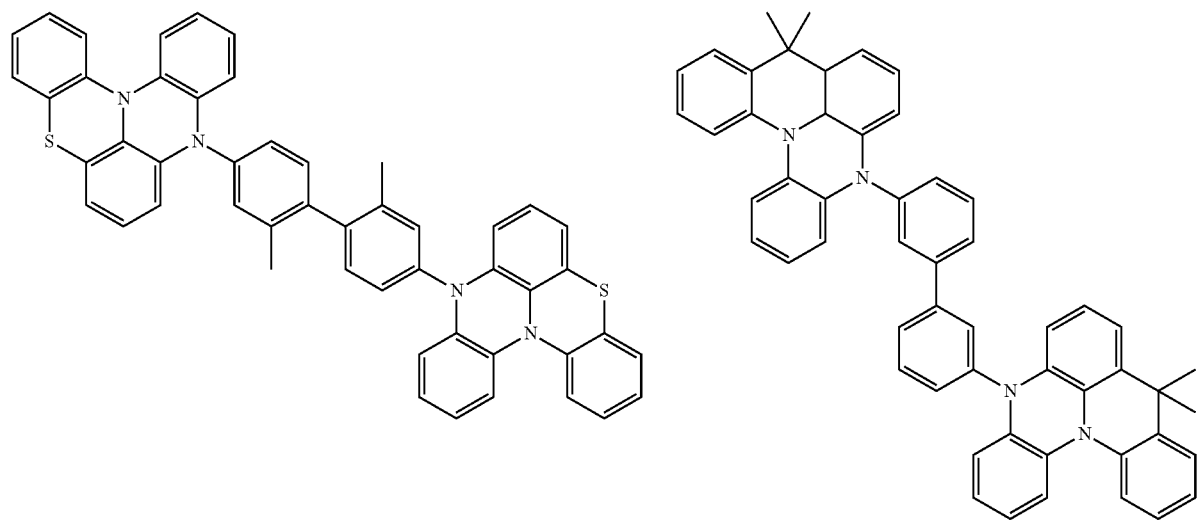
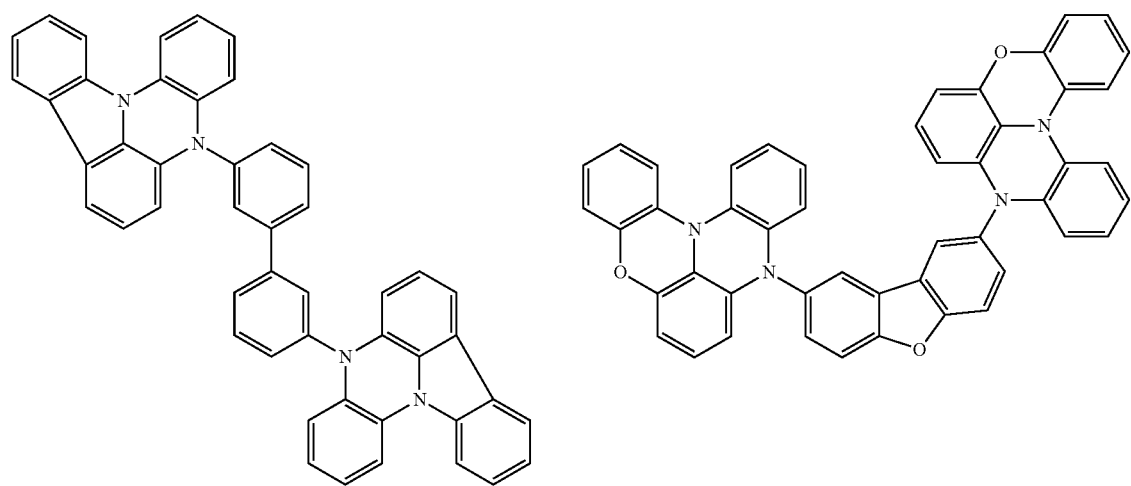

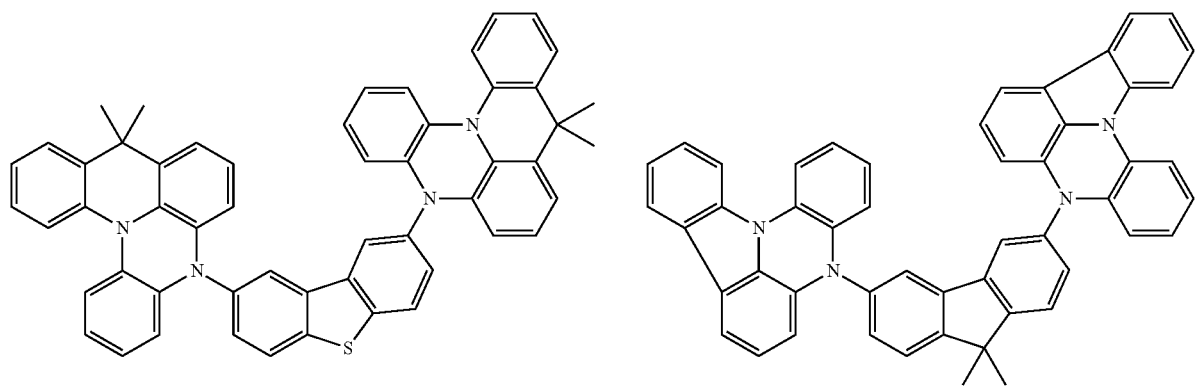
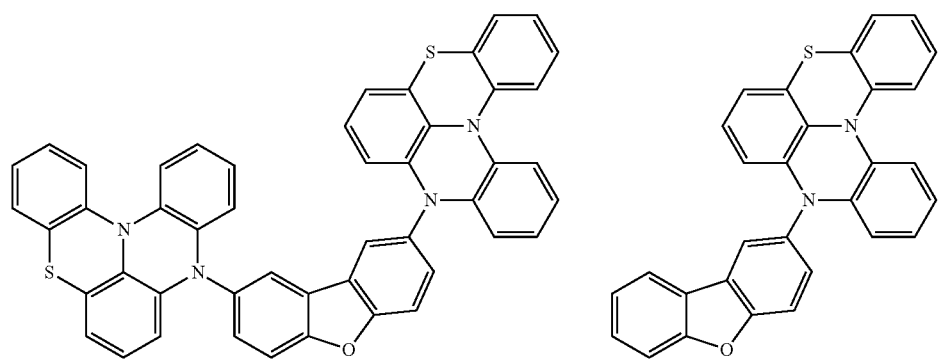
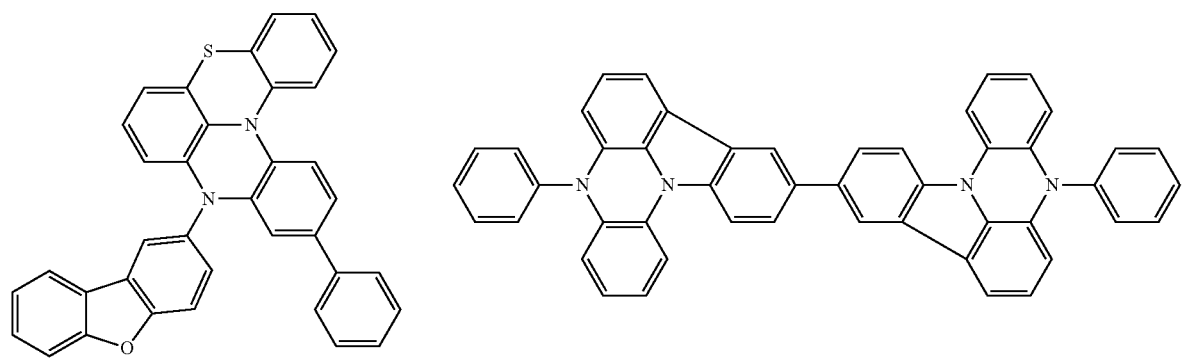
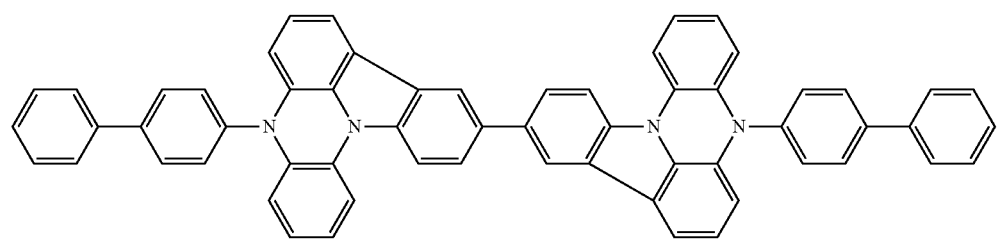

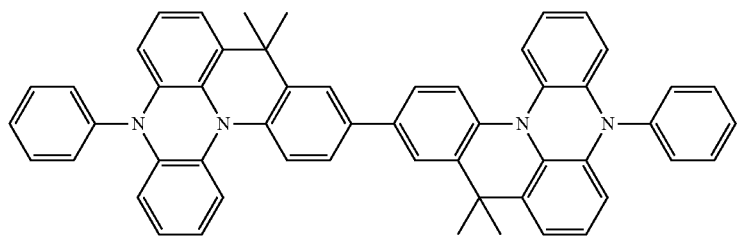
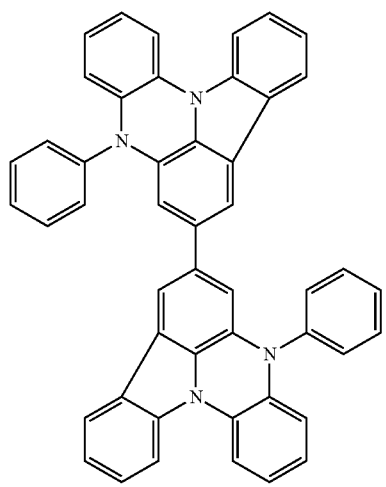
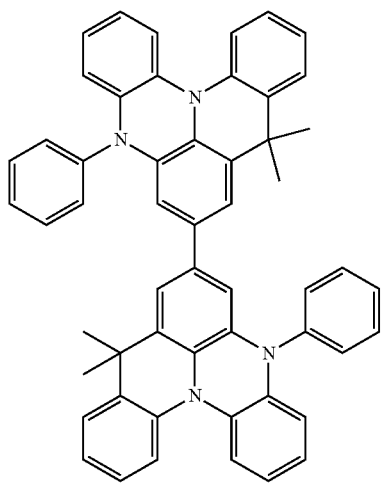
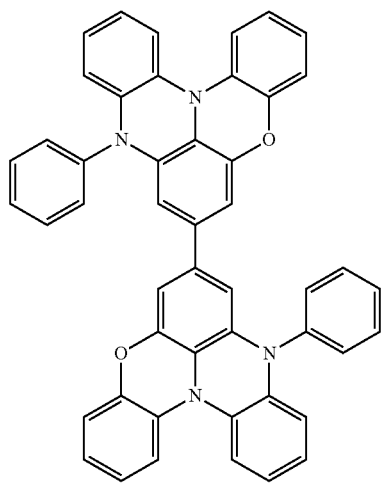
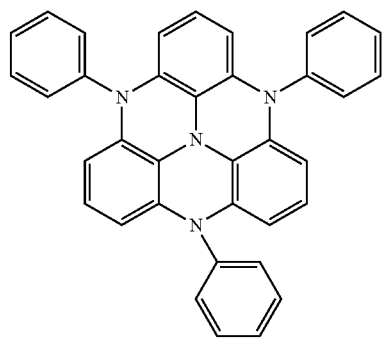
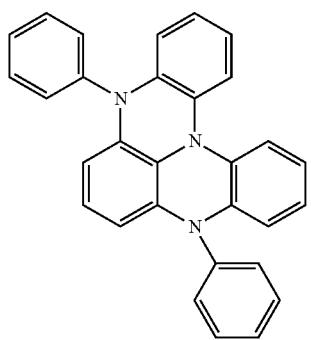
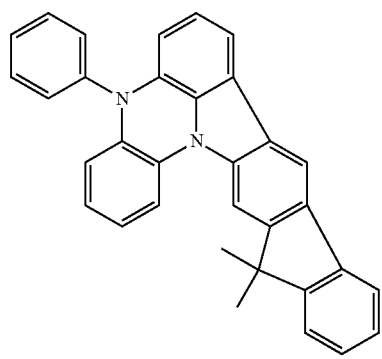
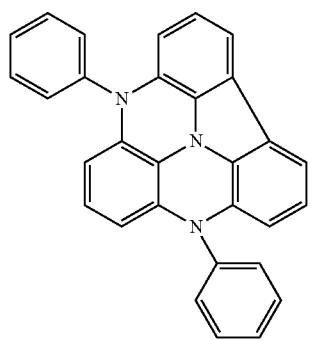

The synthesis of the compounds according to the invention is shown in general terms in Scheme 1 to Scheme 3.
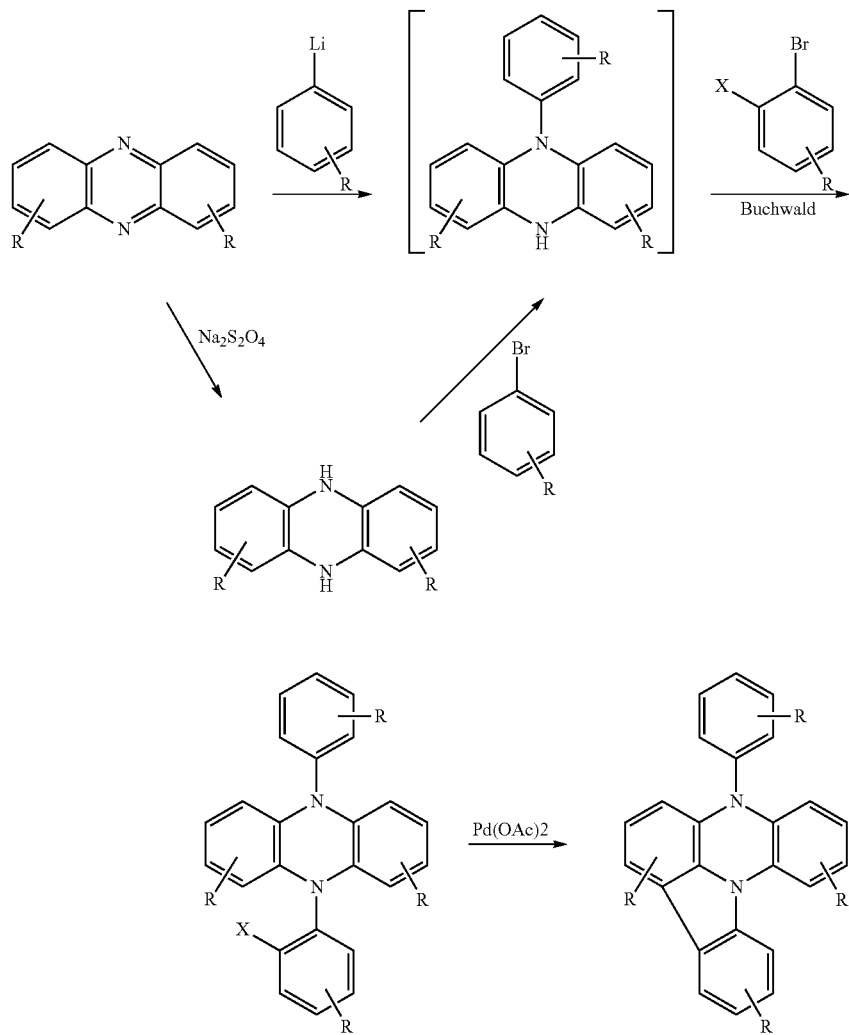
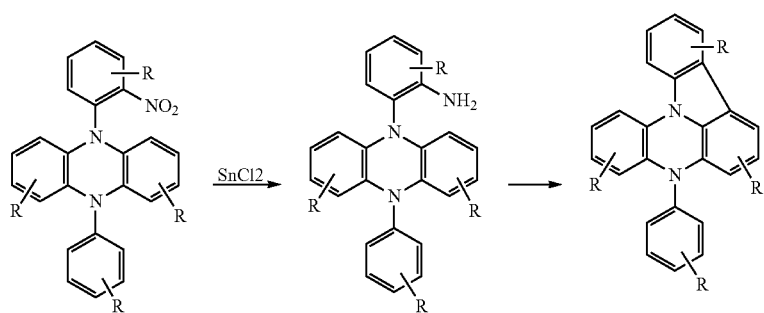

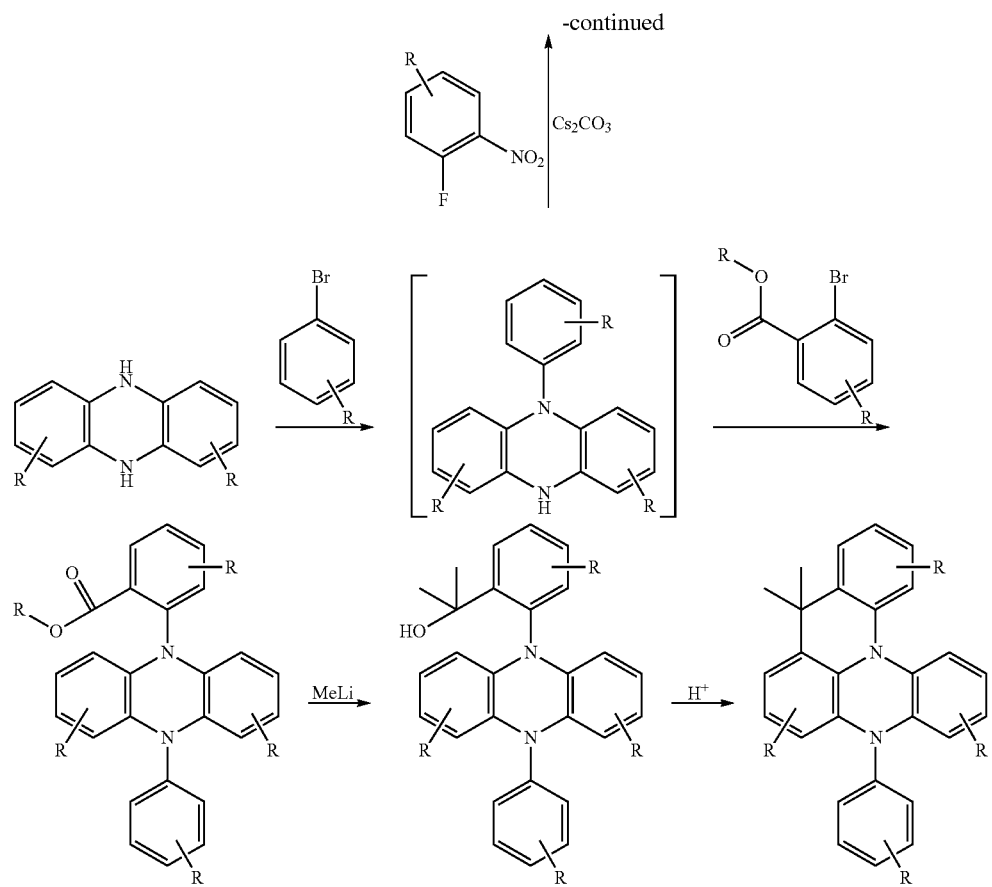
Scheme 3
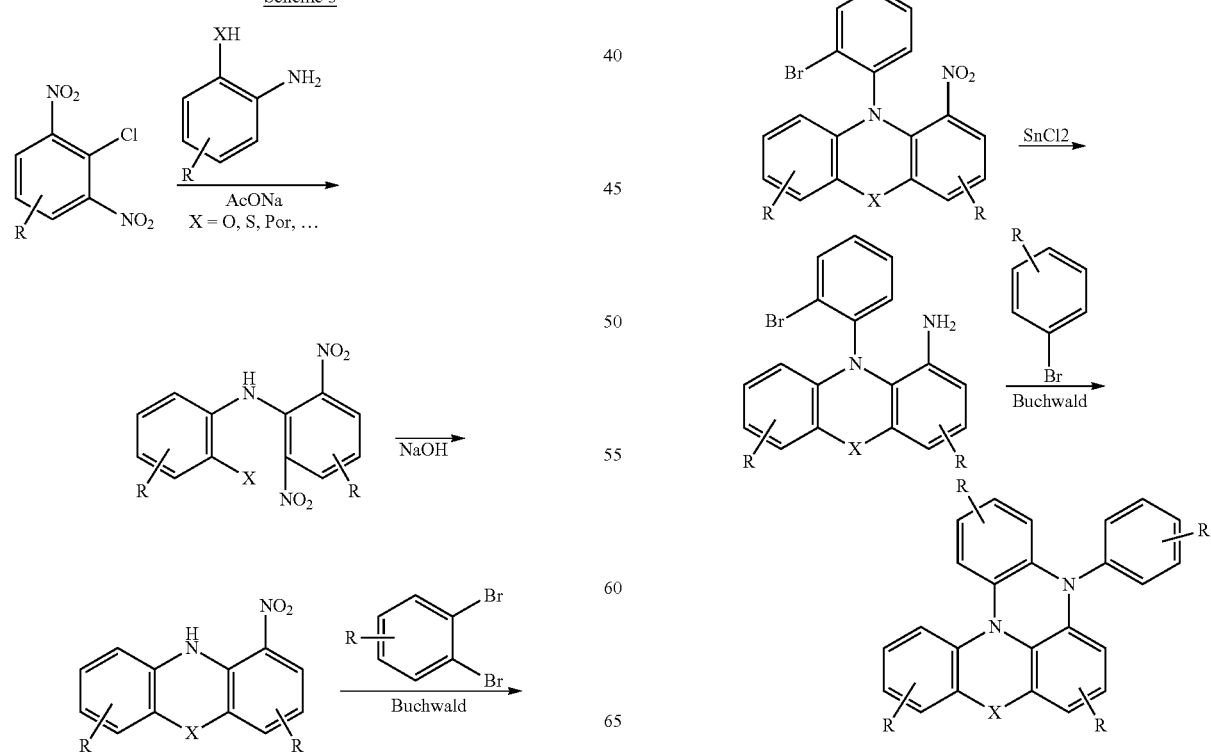

The present invention therefore furthermore relates to a process for the preparation of a compound of the formula (1), comprising the reaction steps:
a) synthesis of the corresponding basic structure which does not yet contain a bridge Y; and
b) introduction of the group Y.

The present invention furthermore relates to mixtures comprising at least one compound according to the invention and at least one further compound. The further compound can be, for example, a fluorescent or phosphorescent dopant if the compound according to the invention is used as matrix material. Suitable fluorescent and phosphorescent dopants are indicated below in connection with the organic electroluminescent devices and are also preferred for the mixtures according to the invention. The further compound can also be a dopant if the compound according to the invention is employed as hole-transport or electron-transport compound. Suitable dopants are indicated below in connection with the organic electroluminescent devices.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, a suspension or a mini-emulsion, comprising at least one compound or mixture according to the invention and one or more solvents, in particular organic solvents. The way in which solutions of this type can be prepared is known to the person skilled in the art and described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the above-mentioned compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound according to the invention as matrix material for fluorescent or phosphorescent emitters, in particular for phosphorescent emitters, and/or in an electron-blocking or exciton-blocking layer and/or in a hole-transport or hole-injection layer. The preferred embodiments indicated above also apply to the use of the materials in organic electronic devices.

In a preferred embodiment of the invention, the compound according to the invention is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound according to the invention is employed as matrix material for an emitting compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052 or the unpublished application EP 11010103.7, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778, WO 2011/042107 or WO 2011/088877. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339 and WO 2012/007086. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound according to the invention is employed as hole-transport or hole-injection material in a hole-transport or hole-injection layer. The emitting layer here may be fluorescent or phosphorescent. A hole-injection layer in the sense of the present invention is a layer which is directly adjacent to the anode. A hole-transport layer in the sense of the present invention is a layer which is located between a hole-injection layer and an emitting layer.

In still a further preferred embodiment of the invention, the compound according to the invention is employed in an exciton-blocking layer. An exciton-blocking layer is taken to mean a layer which is directly adjacent to an emitting layer on the anode side.

If the compound according to the invention are employed in a hole-injection or in a hole-transport layer, they may also be doped, in which case in general all dopants as are usually employed in accordance with the prior art are suitable. Suitable dopants are electron-acceptor compounds, for example $F_4$-TCNQ (tetrafluorotetracyanoquinodimethane) or compounds as described in EP 1476881 or EP 1596445.

In an embodiment of the invention, the compound according to the invention is used in a hole-transport or -injection layer in combination with a layer which comprises a hexaazatriphenylene derivative, in particular hexacyanohexaazatriphenylene (for example in accordance with EP 1175470). Thus, for example, preference is given to a combination which looks as follows: anode-hexaazatriphenylene derivative-hole-transport layer, where the hole-transport layer comprises one or more compounds according to the invention. It is likewise possible in this construction to use a plurality of successive hole-transport layers, where at least one hole-transport layer comprises at least one compound according to the invention. A further preferred combination looks as follows: anode-hole-transport layer-hexaazatriphenylene derivative-hole-transport layer, where at least one of the two hole-transport layers comprises one or more compounds according to the invention. It is likewise possible in this construction for a plurality of successive hole-transport layers to be used instead of one hole-transport layer, where at least one hole-transport layer comprises at least one compound according to the invention.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds according to the invention.

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by one or more of the following surprising advantages:

1. The compounds according to the invention, employed as matrix material for fluorescent or phosphorescent emitters, result in high efficiencies and long lifetimes. This applies, in particular, if the compounds are employed as matrix material for a phosphorescent emitter.
2. The compounds according to the invention have high thermal stability.
3. The compounds according to the invention, employed in organic electroluminescent devices, result in high efficiencies and in steep current/voltage curves with low use voltages.
4. On use as hole-transport material, the compounds according to the invention result in good properties with respect to the efficiency, the lifetime and the operating voltage of organic electroluminescent devices.

These above-mentioned advantages are not accompanied by an impairment in the other electronic properties.

The invention is explained in greater detail by the following examples, without wishing to restrict it thereby. The person skilled in the art will be able to carry out the invention throughout the range disclosed on the basis of the descriptions and prepare further compounds according to the invention without inventive step and use them in electronic devices or use the process according to the invention.

EXAMPLES

The following syntheses are carried out, unless indicated otherwise, in dried solvents under a protective-gas atmosphere. The solvents and reagents can be purchased, for example, from Sigma-ALDRICH or ABCR. The starting material used can be, for example, phenazine. The numbers in square brackets in the case of the starting materials known from the literature relate to the CAS numbers.

Example 1: 5,10-Dihydrophenazine

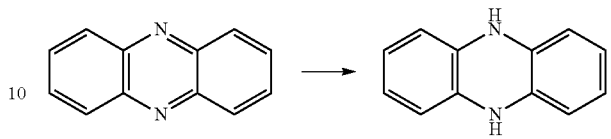

20 g (110 mmol) of phenazine are suspended in 600 ml of ethanol under protective gas. The reaction mixture is heated under reflux. 38.3 g (220 mmol) of sodium dithionite dissolved in 600 ml of degassed water are subsequently added dropwise, and the mixture is heated under reflux for a further 4 h. After cooling, the precipitated yellow solid is filtered off under protective gas and dried in vacuo. The purity is 92.0%. Yield: 19 g (107 mmol) 96% of theory.

Example 2: 5-Biphenyl-4-yl-10-(2-bromophenyl)-5,10-dihydrophenazine

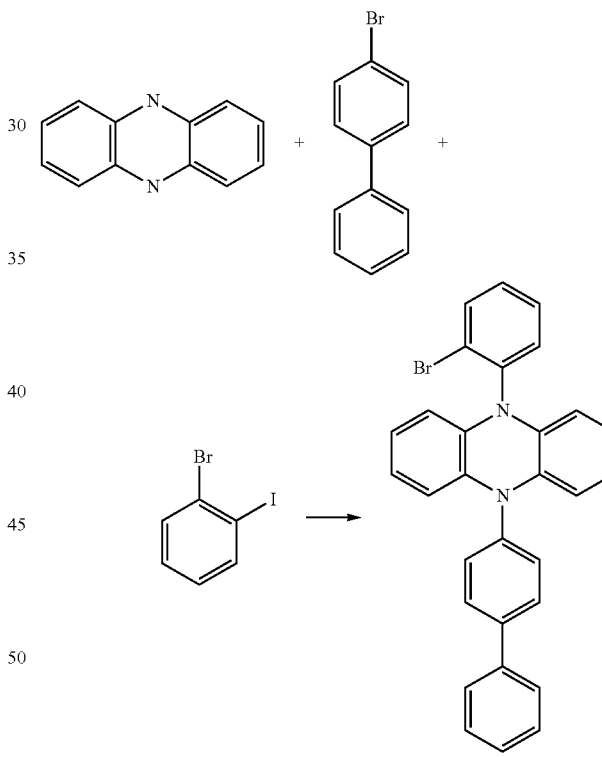

15.8 g (87.8 mmol) of 9,10-dihydrophenazine, 20 g (87 mmol) of 4-bromobiphenyl and 0.8 g (0.88 mmol) of tris(dibenzylideneacetone)dipalladium, 1.79 g (7.9 mmol) of palladium acetate are suspended in 500 ml of toluene under protective gas. The reaction mixture is heated under reflux for 8 h. 24.8 g (87 mmol) of 1-bromo-2-iodobenzene is subsequently added, and the mixture is heated under reflux for a further 8 h. After cooling, the organic phase is separated off, washed three times with 200 ml of water each time and subsequently evaporated to dryness. The product is purified by column chromatography on silica gel with toluene/heptane (1:2). The purity is 97.0%. Yield: 29 g (37 mmol) 70% of theory.

Compounds 2a-2m are obtained analogously:

| Ex. | Starting material 1 | Starting material 2 | Product | Yield |
|---|---|---|---|---|
| 2a | [1,1':3',1''-terphenyl]-5'-yl bromide [103068-20-8] | 1,2-dibromobenzene | 5-(3,5-diphenylphenyl)-10-(2-bromophenyl)-5,10-dihydrophenazine | 65% |
| 2b | bromobenzene | 1,2-dibromobenzene | 5-phenyl-10-(2-bromophenyl)-5,10-dihydrophenazine | 66% |
| 2c | 2-bromobiphenyl [2052-07-5] | 1,2-dibromobenzene | 5-(2-biphenyl)-10-(2-bromophenyl)-5,10-dihydrophenazine | 73% |
| 2d | 1,2-dibromobenzene | 1,2-dibromobenzene | 5,10-bis(2-bromophenyl)-5,10-dihydrophenazine | |

-continued
| Ex. | Starting material 1 | Starting material 2 | Product | Yield |
|---|---|---|---|---|
| 2f | 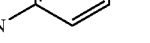 [586-78-7] | 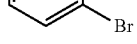 | 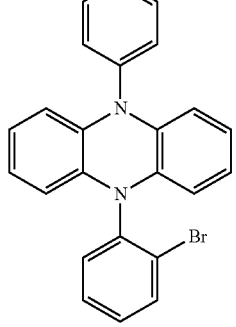 | 75% |
| 2g | 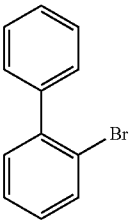 [SMILES: Brc1ccccc1-c1ccccc1] | 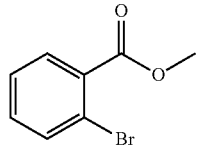 [610-94-6] | 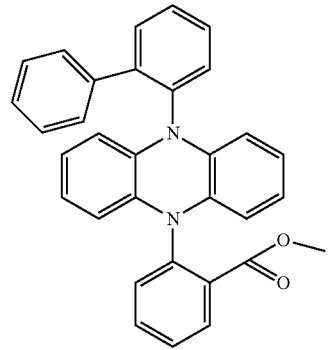 | 65% |
| 2h | 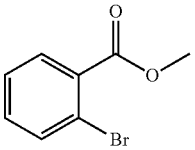 | 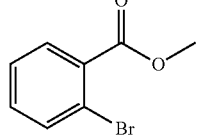 | 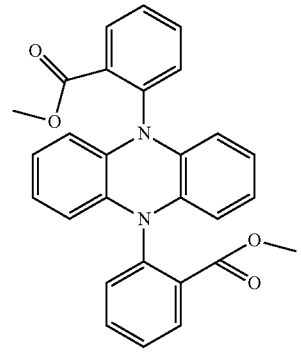 | 87% |
| 2i | 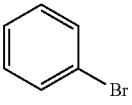 | 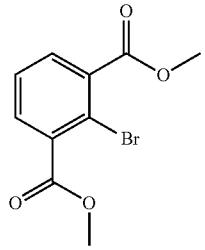 | 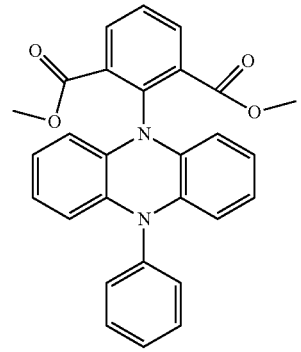 | 63% |

| Ex. | Starting material 1 | Starting material 2 | Product | Yield |
|---|---|---|---|---|
| 2j | 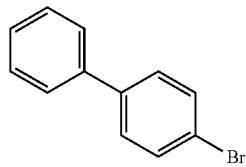 [SMILES: Brc1ccc(-c2ccccc2)cc1] | 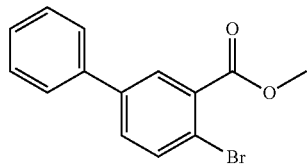 [SMILES: COC(=O)c1cc(-c2ccccc2)ccc1Br]  [727408-92-6] | 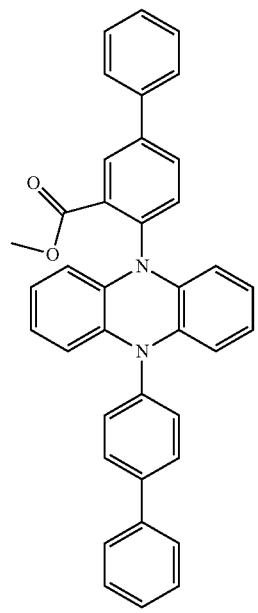 [SMILES: COC(=O)c1cc(-c2ccccc2)ccc1N1c2ccccc2N(c2ccc(-c3ccccc3)cc2)c2ccccc21] | 72% |
| 2k | 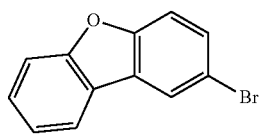 [SMILES: Brc1ccc2oc3ccccc3c2c1]  [86-76-0] | 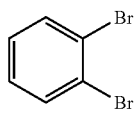 | 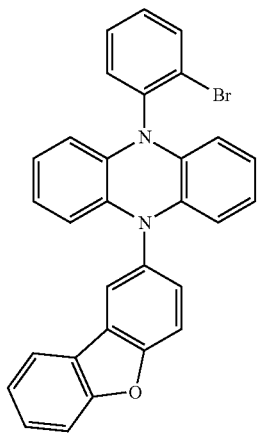 [SMILES: Brc1ccccc1N1c2ccccc2N(c2ccc3oc4ccccc4c3c2)c2ccccc21] | 67% |

-continued
| Ex. | Starting material 1 | Starting material 2 | Product | Yield |
|---|---|---|---|---|
| 2l | 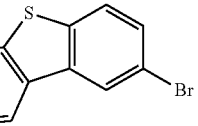 [22439-61-8] | 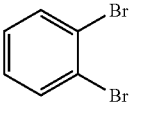 | 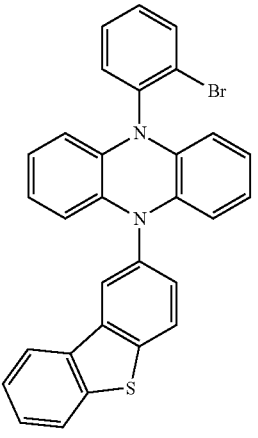 | 69% |
| 2m | 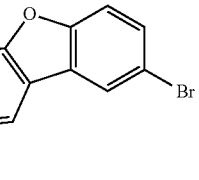 [10016-52-1] | 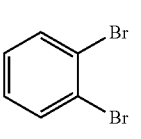 | 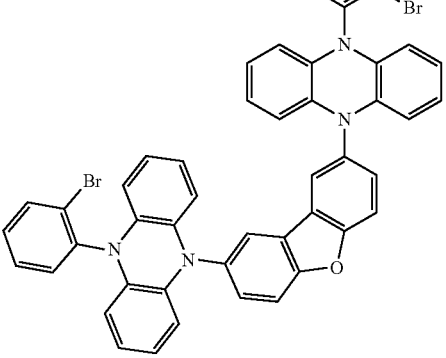 | 63% |
Compound 2n is obtained analogously:
| Ex. | Starting material 1 | Starting material 2 | Starting material 3 | Product | Yield |
|---|---|---|---|---|---|
| 2n | 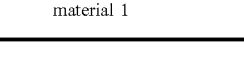 [19029-32-4] | 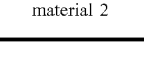 | 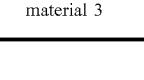 | 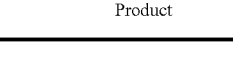 | 69% |

Example 3: 8-Biphenyl-4-yl-8H-8,12b-diazabenzo[a]aceanthrylene

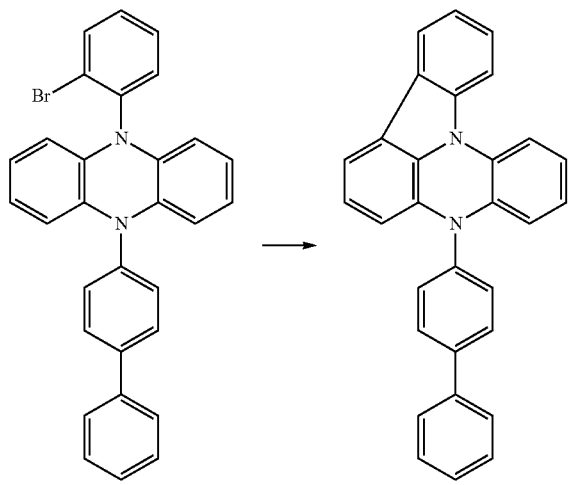 [SMILES: Brc1ccccc1N1c2ccccc2N(c2ccc(-c3ccccc3)cc2)c2ccccc21 ; c1ccc(-c2ccc(N3c4ccccc4-n4c5ccccc5c5cccc3c54)cc2)cc1]

73 g (0.175 mmol) of 5-biphenyl-4-yl-10-(2-bromophenyl)-5,10-dihydrophenazine are dissolved in 500 ml of dimethylacetamide under protective gas. 2.4 g (6.5 mmol) of tricyclohexylphosphine tetrafluoroborate and 701 mg (3.1 mmol) of Pd(OAc)$_2$ are added to this solution. The mixture is subsequently stirred at 120° C. for 9 h. After this time, the reaction mixture is cooled to room temperature and extracted with dichloromethane. The combined organic phases are dried over Na$_2$SO$_4$ and evaporated. The residue is extracted with hot toluene, recrystallised from toluene and finally sublimed in a high vacuum. The yield is 49 g (121 mmol), 81% of theory.

Compounds 3a-3m are obtained analogously:

| Ex. | Starting material 1 | Product | Yield |
|---|---|---|---|
| 3a |  |  | 75% |
| 3b |  |  | 76% |

-continued

| Ex. | Starting material 1 | Product | Yield |
|---|---|---|---|
| 3c | | | 73% |
| 3e | | | 40% |
| 3g | | | 76% |
| 3h | | | 31% |

-continued

| Ex. | Starting material 1 | Product | Yield |
|---|---|---|---|
| 3i | | | 29% |
| 3j | | | 20% |
| 3k | | | 71% |
| 3l | | | 69% |

| Ex. | Starting material 1 | Product | Yield |
|---|---|---|---|
| 3m | | | 72% |

Example 4: 2-[2-(10-Biphenyl-2-yl-10H-phenazin-5-yl)phenyl]propan-2-ol 99 g (213 mmol) of methyl 2-(10-biphenyl-2-yl-10H-phenazin-5-yl)benzoate are dissolved in 1500 ml of dried THF and degassed. The mixture is cooled to −78° C., and 569 ml (854 mmol) of methyllithium are added over the course of 40 min. The mixture is allowed to warm to −40° C. over the course of 1 h, and the reaction is monitored by TLC. When the reaction is complete, the mixture is carefully quenched with MeOH at −30° C. The reaction solution is evaporated to ⅓, and 1 l of $CH_2Cl_2$ is added, the mixture is washed, and the organic phase is dried over $MgSO_4$ and evaporated. The yield is 90 g (194 mmol) 90% of theory.

Compounds 4a-4c are obtained analogously

| Ex. | Starting material 1 | Product | Yield |
|---|---|---|---|
| 4a | | | 87% |
| 4b | | | 67% |

-continued

| Ex. | Starting material 1 | Product | Yield |
|---|---|---|---|
| 4c | | | 74% |

Example 5: 5-Biphenyl-2-yl-9,9-dimethyl-5H,9H-5,13b-diazanaphtho[3,2,1-de]anthracene

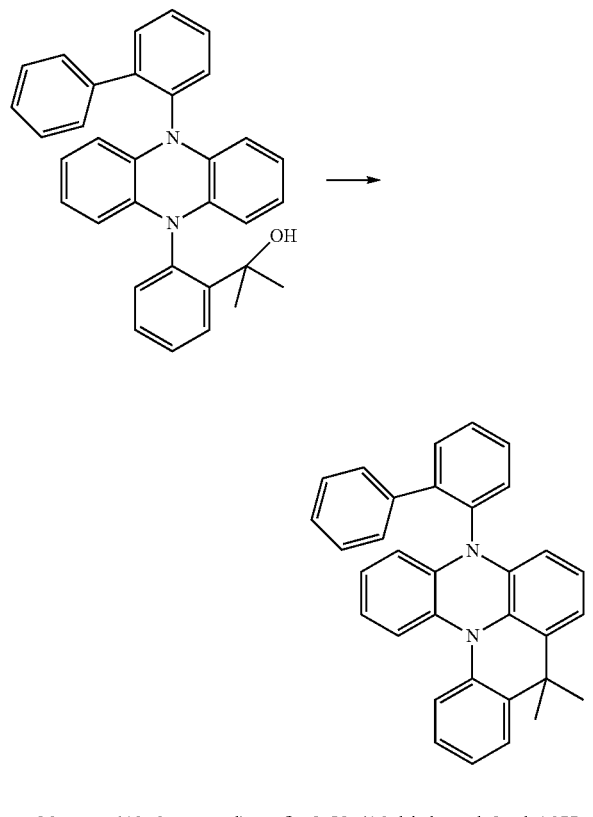

20 g (43.6 mmol) of 2-[2-(10-biphenyl-2-yl-10H-phenazin-5-yl)phenyl]propan-2-ol are dissolved in 1200 ml of degassed toluene, and a suspension of 40 g of polyphosphoric acid and 28 ml of methanesulfonic acid is added, and the mixture is heated at 60° C. for 1 h. The batch is cooled, and water is added. A solid precipitates out, which is dissolved in $CH_2Cl_2$/THF (1:1). The solution is carefully rendered alkaline using 20% NaOH, the phases are separated and dried over $MgSO_4$. The residue is extracted with hot toluene, recrystallised from toluene/heptane (1:2) and finally sublimed in a high vacuum. The yield is 15.6 g (34 mmol), 80% of theory.

Compounds 5a-5d are obtained analogously:

| Ex. | Starting material 1 | Product | Yield |
|---|---|---|---|
| 5a | | | 43% |
| 5b | | | 33% |
| 5c | | | 68% |

-continued

| Ex. | Starting material 1 | Product | Yield |
|---|---|---|---|
| 5d | 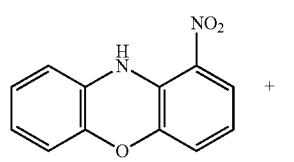 | 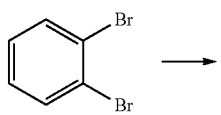 | 69% |

Example 6:
1-Nitro-10-(2-bromophenyl)-10H-phenoxazine

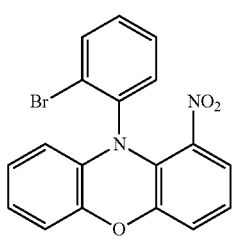

20 g (88 mmol) of 1-nitro-10H-phenoxazine (CAS: 26103-27-5), 20 g (88 mmol) of 1,2-dibromobenzene, 0.8 g (0.88 mmol) of tris(dibenzylideneacetone)dipalladium and 1.79 g (7.9 mmol) of palladium acetate are suspended in 500 ml of toluene under protective gas. The reaction mixture is heated under reflux for 8 h. After cooling, the organic phase is separated off, washed three times with 200 ml of water and subsequently evaporated to dryness. The product is purified by column chromatography on silica gel with toluene/heptane (1:2). The purity is 97.0%. Yield: 19 g (49 mmol), 78% of theory.

Compounds 6a-6b are obtained analogously:

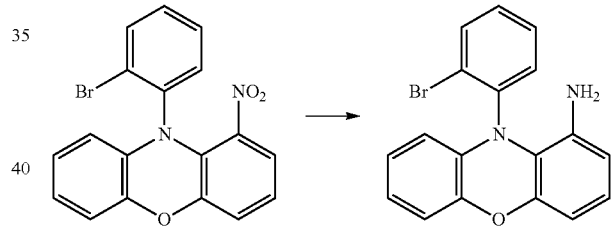

Example 7:
10-(2-Bromophenyl)-10H-phenoxazin-1-ylamine 14.5 g (42 mmol) of 1-nitro-10-(2-bromophenyl)-10H-phenoxazine is suspended in 200 ml of ethanol. 26 g (140 mmol) of SnCl$_2$ dissolved in 25 ml of conc. HCl are added in portions at 60° C. with stirring, and the mixture is heated under reflux for 8 h. The precipitate is then filtered off and dried in vacuo. The purity is 94%. Yield: 12 g (35 mmol), 92% of theory.

Compounds 7a-7b are obtained analogously:

| Ex. | Starting material 1 | Product | Yield |
|---|---|---|---|
| 7b | 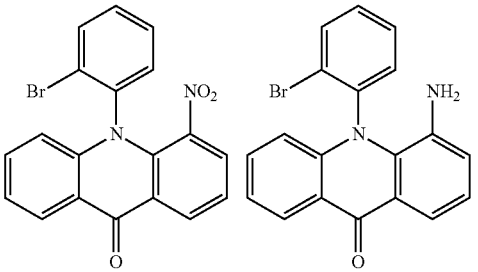 | 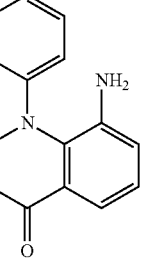 | 81% |

Example 8: 9-Phenyl-9H-5-oxa-9,13b-diazanaphtho[3,2,1-de]anthracene

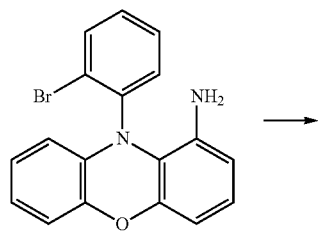 →

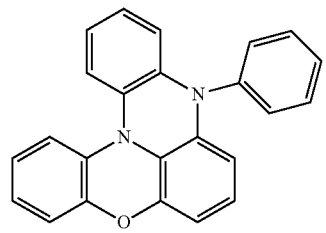

9.2 g (26.3 mmol) of 9,10-dihydrophenazine, 0.24 g (0.26 mmol) of tris(dibenzylideneacetone)dipalladium and 0.53 g (2.37 mmol) of palladium acetate are suspended in 150 ml of toluene under protective gas. The reaction mixture is heated under reflux for 8 h. 4 g (26 mmol) of 4-bromobenzene are subsequently added, and the mixture is heated under reflux for a further 8 h. After cooling, the organic phase is separated off, washed three times with 80 ml of water and subsequently evaporated to dryness. The residue is extracted with hot toluene, recrystallised from toluene/heptane (1:2) and finally sublimed in a high vacuum. The purity is 97.0%. Yield: 5.6 g (16.3 mmol) 63% of theory.

Compounds 8a-8f are obtained analogously:

| Ex. | Starting material 1 | Starting material 2 | Product | Yield |
|---|---|---|---|---|
| 8a | | | | 64% |

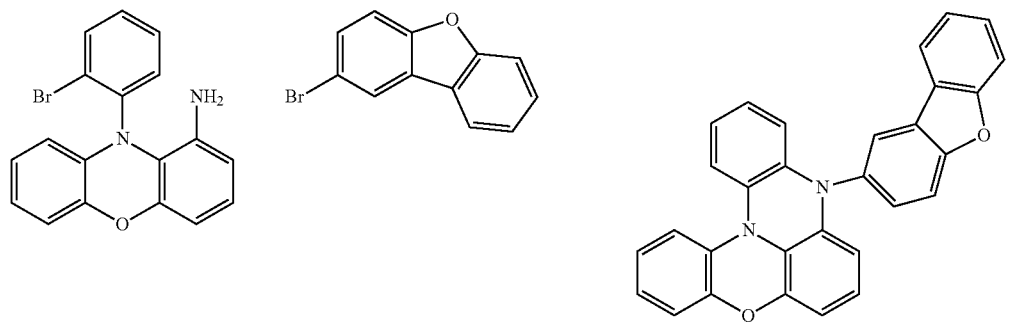

| 8b | | | | 59% |

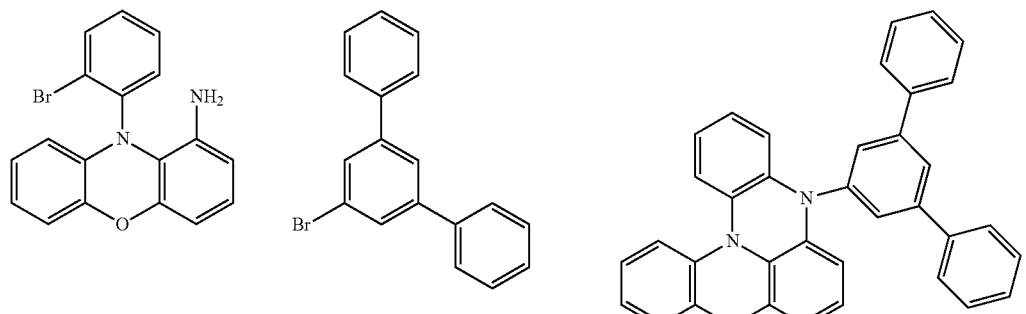

[103068-20-8]

-continued

| Ex. | Starting material 1 | Starting material 2 | Product | Yield |
|---|---|---|---|---|
| 8c | 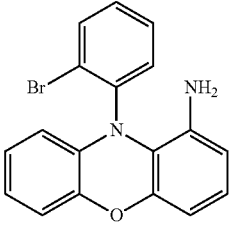 [SMILES: Nc1cccc2c1N(c1ccccc1Br)c1ccccc1O2] | 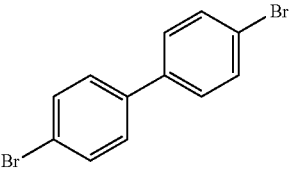 [SMILES: Brc1ccc(-c2ccc(Br)cc2)cc1] | 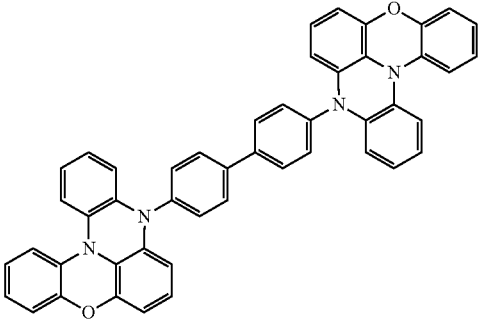 [SMILES: c1ccc2c(c1)Oc1cccc3c1N2c1ccccc1N3c1ccc(-c2ccc(N3c4ccccc4N4c5ccccc5Oc5cccc3c54)cc2)cc1] | 53% |
| 8e | 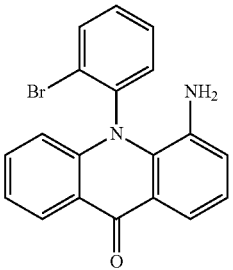 [SMILES: Nc1cccc2c(=O)c3ccccc3n(-c3ccccc3Br)c12] | 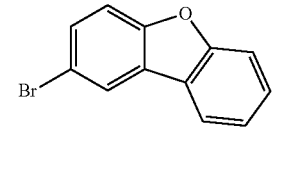 [SMILES: Brc1ccc2oc3ccccc3c2c1] | 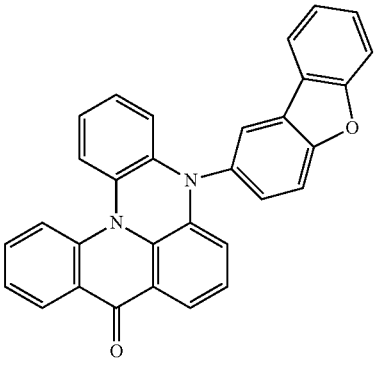 [SMILES: O=c1c2ccccc2n2c3c(cccc13)N(c1ccc3oc4ccccc4c3c1)c1ccccc1-2] | 58% |
| 8f | 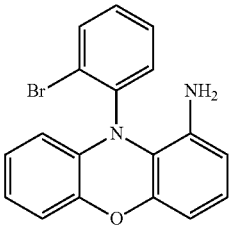 [SMILES: Nc1cccc2c1N(c1ccccc1Br)c1ccccc1O2] | 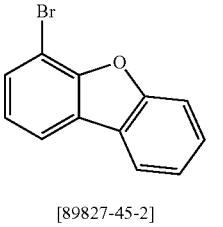 [89827-45-2] | 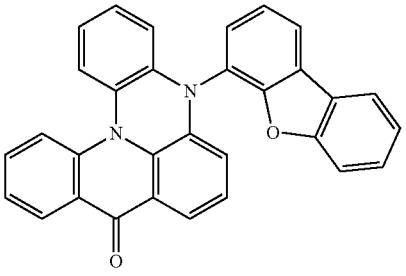 [SMILES: O=c1c2ccccc2n2c3c(cccc13)N(c1cccc3c1oc1ccccc13)c1ccccc1-2] | 55% |

Example 9: Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in the following Examples V1 to E17 (see Tables 1 and 2). Glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied. The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium cathode with a thickness of 100 nm. The precise structure of the OLEDs is shown in Table 1. The materials required for the production of the OLEDs are shown in Table 1. Furthermore, a reference to the materials such as "3f" relates to the material whose synthesis is described in Example 3f indicated above. This applies analogously to the other compounds according to the invention.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as IC1:3k:TEG1 (70%: 25%:5%) here means that material IC1 is present in the layer in a proportion by volume of 70%, the material from Example 3k is present in the layer in a proportion of 25% by vol. and TEG1 is present in the layer in a proportion of 15% by vol. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), assuming Lambert emission characteristics, and the lifetime are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiencies achieved at 1000 cd/m$^2$, Finally, EQE1000 denotes the external quantum efficiency at an operating luminous density of 1000 cd/m$^2$.

The data of the various OLEDs are summarised in Table 2. Example V1-V3 are comparative examples in accordance with the prior art, Examples E1-E17 show data of OLEDs comprising materials according to the invention.

Some of the examples are explained in greater detail below in order to illustrate the advantages of the compounds according to the invention. However, it should be pointed out that this only represents a selection of the data shown in Table 2.

Use of Compounds According to the Invention as Hole-Transport Materials

If compound 3f according to the invention is used instead of the similar compound H3 in accordance with the prior art as hole-transport material in an OLED comprising the green dopant TEG1, a virtually 20% better power efficiency is obtained (Examples V1 and E5).

Use of Compounds According to the Invention as Matrix Materials in Phosphorescent OLEDs The use of two materials as matrix (host) in OLEDs comprising green-phosphorescent dopants frequently gives rise to better performance data than on use of a single material, which is why materials are of great interest for this application. Inter alia, materials according to the invention containing sulfur- or oxygen-containing heteroaromatic ring systems as substituent are distinguished here compared with triazine-containing materials in accordance with the prior art: better quantum and power efficiency (Examples V2, V3, E6, E7 and E8) are obtained. Furthermore, the lifetime is significantly improved. While the luminous density drops to 70% from its initial value of 10000 cd/m$^2$ within 160 h and 180 h respectively for Examples V2 and V3 on operation at constant current density, this takes 300 h, 245 h and 230 h in Examples E6, E7 and E8 respectively.

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| V1 | — | SpA1 70 nm | HATCN 5 nm | H3 90 nm | IC1:TEG1 (90%:10%) 30 nm | — | ST1:LiQ (50%:50%) 40 nm | — |
| V2 | — | SpA1 70 nm | HATCN 5 nm | SpMA1 90 nm | IC1:H1:TEG1 (70%:25%:5%) 30 nm | IC1 10 nm | ST1:LiQ (50%:50%) 30 nm | — |
| V3 | — | SpA1 70 nm | HATCN 5 nm | SpMA1 90 nm | IC1:H2:TEG1 (70%:25%:5%) 30 nm | IC1 10 nm | ST1:LiQ (50%:50%) 30 nm | — |
| E1 | — | SpA1 90 nm | HATCN 5 nm | SpMA1 130 nm | IC5:3c:TER1 (43%:50%:7%) 40 nm | — | ST2:LiQ (50%:50%) 40 nm | — |
| E2 | — | SpA1 90 nm | HATCN 5 nm | SpMA1 130 nm | IC5:3i:TER1 (33%:60%:7%) 40 nm | — | ST2:LiQ (50%:50%) 40 nm | — |
| E3 | — | SpA1 90 nm | HATCN 5 nm | SpMA1 130 nm | IC5:5:TER1 (43%:50%:7%) 40 nm | — | ST2:LiQ (50%:50%) 40 nm | — |
| E4 | — | SpA1 90 nm | HATCN 5 nm | SpMA1 130 nm | IC5:5d:TER1 (53%:40%:7%) 40 nm | IC1 10 nm | ST2:LiQ (50%:50%) 30 nm | — |
| E5 | — | SpA1 70 nm | HATCN 5 nm | 3m 90 nm | IC1:TEG1 (90%:10%) 30 nm | — | ST1:LiQ (50%:50%) 40 nm | — |
| E6 | — | SpA1 70 nm | HATCN 5 nm | SpMA1 90 nm | IC1:3k:TEG1 (70%:25%:5%) 30 nm | IC1 10 nm | ST1:LiQ (50%:50%) 30 nm | — |
| E7 | — | SpA1 70 nm | HATCN 5 nm | SpMA1 90 nm | IC1:3l:TEG1 (70%:25%:5%) 30 nm | IC1 10 nm | ST1:LiQ (50%:50%) 30 nm | — |
| E8 | — | SpA1 70 nm | HATCN 5 nm | SpMA1 90 nm | IC1:3m:TEG1 (70%:25%:5%) 30 nm | IC1 10 nm | ST1:LiQ (50%:50%) 30 nm | — |
| E9 | HATCN 5 nm | 3a 140 nm | HATCN 5 nm | SpMA1 20 nm | M2:D1 (95%:5%) 20 nm | — | ST1:LiQ (50%:50%) 30 nm | LiQ 1 nm |
| E10 | HATCN 5 nm | 5a 140 nm | HATCN 5 nm | SpMA1 20 nm | M2:D1 (95%:5%) 20 nm | — | ST1:LiQ (50%:50%) 30 nm | LiQ 1 nm |
| E11 | — | 5c 70 nm | HATCN 5 nm | SpMA1 90 nm | IC1:TEG1 (90%:10%) 30 nm | — | ST1:LiQ (50%:50%) 40 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E12 | HATCN 5 nm | 8a 140 nm | HATCN 5 nm | SpMA1 20 nm | M2:D1 (95%:5%) 20 nm | — | ST1:LiQ (50%:50%) 30 nm | LiQ 1 nm |
| E13 | HATCN 5 nm | 8b 140 nm | HATCN 5 nm | SpMA1 20 nm | M2:D1 (95%:5%) 20 nm | — | ST1:LiQ (50%:50%) 30 nm | LiQ 1 nm |
| E14 | HATCN 5 nm | 8c 140 nm | HATCN 5 nm | SpMA1 20 nm | M2:D1 (95%:5%) 20 nm | — | ST1:LiQ (50%:50%) 30 nm | LiQ 1 nm |
| E15 | HATCN 5 nm | 8d 140 nm | HATCN 5 nm | SpMA1 20 nm | M2:D1 (95%:5%) 20 nm | — | ST1:LiQ (50%:50%) 30 nm | LiQ 1 nm |
| E16 | — | 8b 70 nm | HATCN 5 nm | SpMA1 90 nm | IC1:TEG1 (90%:10%) 30 nm | — | ST1:LiQ (50%:50%) 40 nm | — |

TABLE 2

Data of the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| V1 | 3.7 | 55 | 47 | 15.3% | 0.33/0.62 |
| V2 | 3.7 | 53 | 45 | 14.8% | 0.33/0.62 |
| V3 | 3.8 | 45 | 37 | 12.7% | 0.32/0.61 |
| E1 | 4.7 | 10.8 | 7.2 | 11.7% | 0.67/0.33 |
| E2 | 5.1 | 11.7 | 7.2 | 12.6% | 0.67/0.33 |
| E3 | 4.9 | 10.4 | 6.7 | 11.3% | 0.67/0.33 |
| E4 | 4.7 | 10.0 | 6.7 | 10.8% | 0.67/0.33 |
| E5 | 3.4 | 59 | 55 | 16.5% | 0.33/0.62 |
| E6 | 3.9 | 57 | 46 | 15.8% | 0.33/0.62 |
| E7 | 3.5 | 60 | 53 | 16.7% | 0.33/0.62 |
| E8 | 3.6 | 56 | 49 | 16.0% | 0.31/0.61 |
| E9 | 4.3 | 9.5 | 6.9 | 7.4% | 0.14/0.15 |
| E10 | 4.4 | 10.2 | 7.2 | 7.8% | 0.14/0.16 |
| E11 | 3.6 | 57 | 51 | 16.1% | 0.32/0.62 |
| E12 | 4.5 | 10.1 | 7.1 | 7.8% | 0.14/0.16 |
| E13 | 4.1 | 9.1 | 6.9 | 7.0% | 0.14/0.16 |
| E14 | 4.2 | 10.5 | 7.8 | 8.1% | 0.14/0.16 |
| E15 | 4.3 | 9.5 | 7.0 | 7.3% | 0.14/0.16 |
| E16 | 3.5 | 58 | 52 | 15.8% | 0.33/0.62 |

TABLE 3

Structural formulae of the materials for the OLEDs

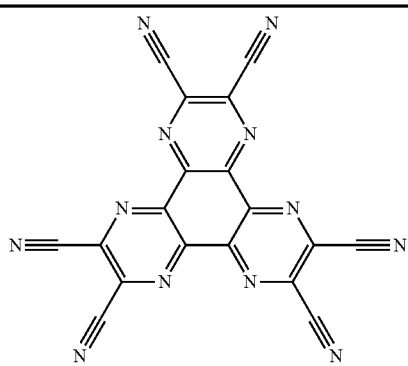

HATCN

SpA1

M2

D1

TABLE 3-continued
Structural formulae of the materials for the OLEDs
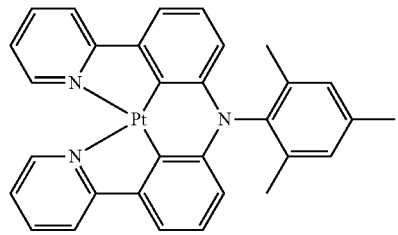
TER1
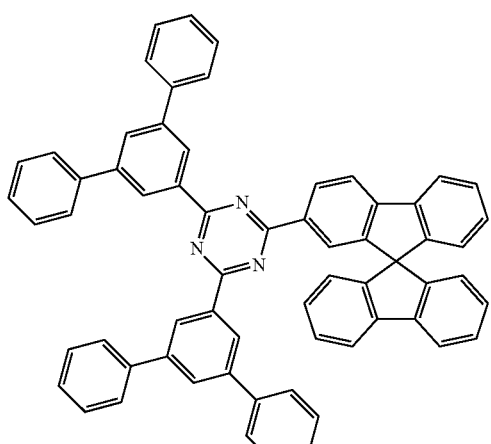
ST1
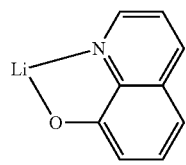
LiQ
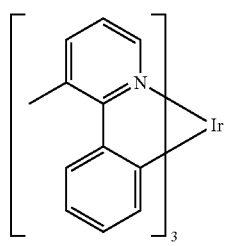
TEG1
TABLE 3-continued
Structural formulae of the materials for the OLEDs
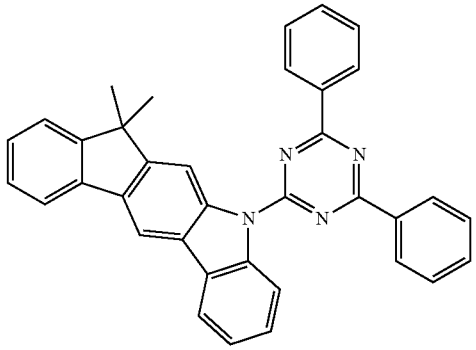 [SMILES: CC1(C)c2ccccc2-c2cc3c4ccccc4n(-c4nc(-c5ccccc5)nc(-c5ccccc5)n4)c3cc21]
IC1
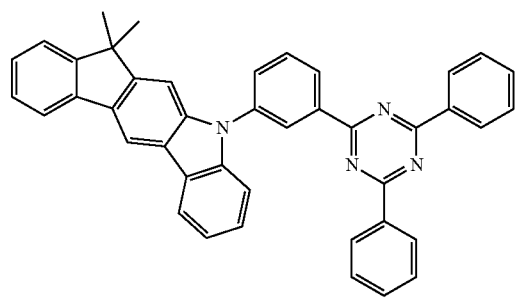 [SMILES: CC1(C)c2ccccc2-c2cc3c4ccccc4n(-c4cccc(-c5nc(-c6ccccc6)nc(-c6ccccc6)n5)c4)c3cc21]
IC5
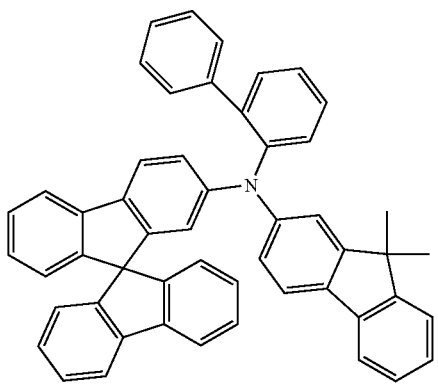 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
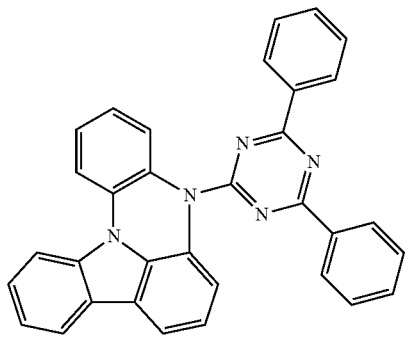 [SMILES: c1ccc(-c2nc(-c3ccccc3)nc(N3c4ccccc4-n4c5ccccc5c5cccc3c54)n2)cc1]
H1 (prior art)

TABLE 3-continued
Structural formulae of the materials for the OLEDs
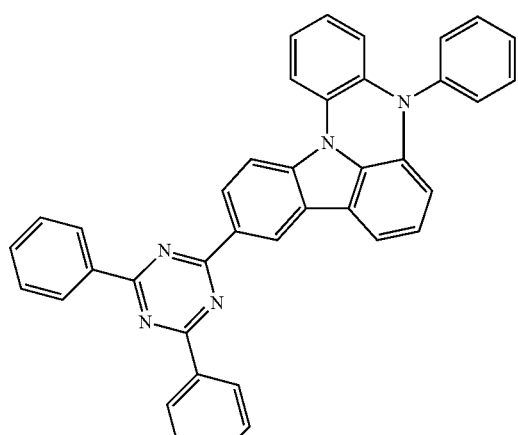
H2 (prior art)
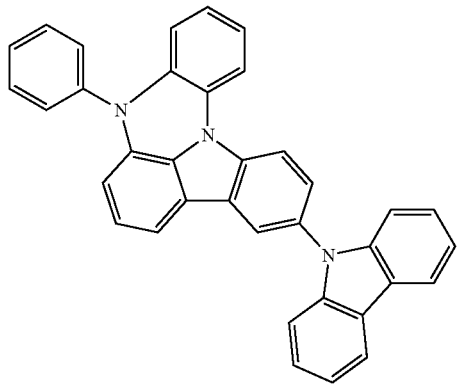 [SMILES: c1ccc(N2c3ccccc3-n3c4ccc(-n5c6ccccc6c6ccccc65)cc4c4cccc2c43)cc1]
H3 (prior art)
The invention claimed is:
1. A compound of the formula (4), (5), (7), (8), and (19)-(22)
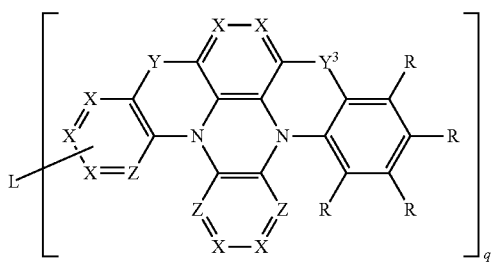
Formula (4)
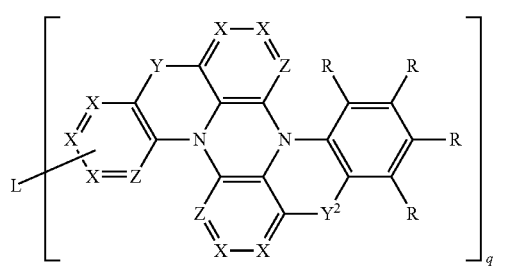
Formula (5)
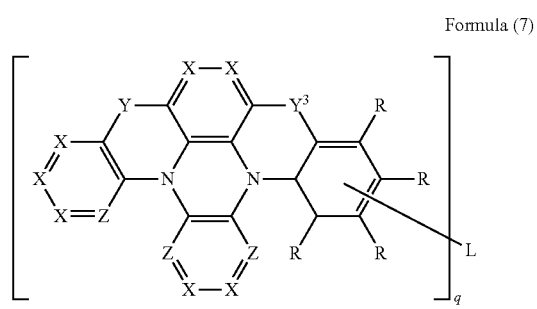
Formula (7)
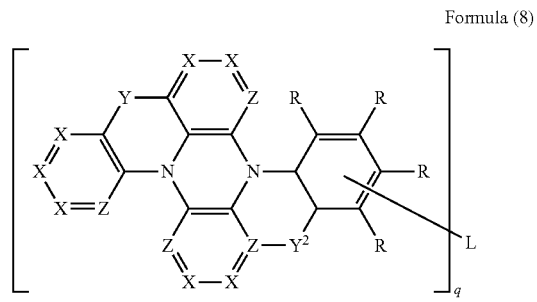
Formula (8)
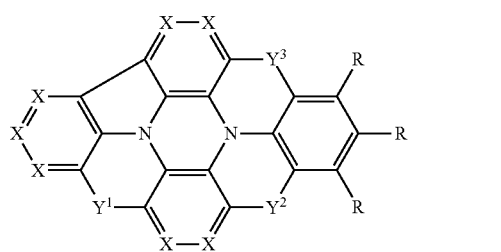
Formula (19)
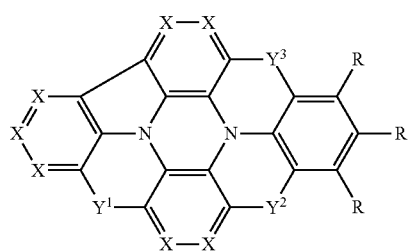
Formula (20)

Formula (21)

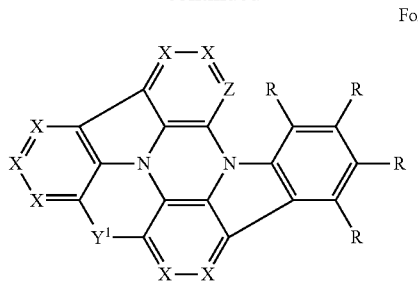

Formula (22)

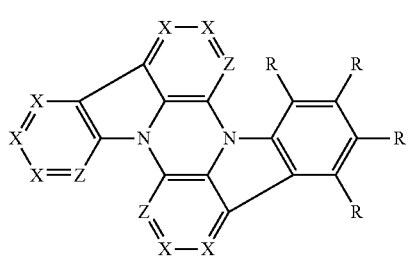

where the following applies to the symbols and indices used:

X is on each occurrence, identically or differently, CR; or X stands for C if a group L is bonded to this group X;

Y, $Y^1$, $Y^2$ and $Y^3$ is on each occurrence, identically or differently, $C(R^1)_2$;

Z is on each occurrence, identically or differently, CR or N; or Z stands for C if a group $Y^1$ or $Y^2$ or $Y^3$ is bonded to this group Z;

a group R is replaced by L in the formula (7) and (8) if the group L is bonded in the corresponding carbon atom;

L is, identically or differently, R if q=1 or is a di-, tri-, tetra-, penta- or hexavalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, which may be substituted by in each case one or more radicals $R^2$, where in each case one or more non-adjacent CH$_2$ groups may be replaced by —$R^2$C=C$R^2$—, —C≡C, Si($R^2$)$_2$, C=O, C=N$R^2$, P(=O)$R^2$, S=O, SO$_2$, —O—, —S— or —CONR$^2$— and where one or more H atoms may be replaced by D, F, Cl, Br, I, CN or NO$_2$, or a di-, tri-, tetra-, penta- or hexavalent aromatic ring system having 5 to 40, aromatic ring atoms, which may be substituted by one or more radicals $R^2$, or heteroaromatic ring system having 5 to 60 aromatic ring atoms, which contains, as heteroaryl groups, exclusively sulfur-containing or oxygen-containing heteroaryl groups and which may be substituted by one or more radicals $R^2$, or P($R^2$)$_{3-r}$, P(=O)($R^2$)$_{3-r}$, C($R^2$)$_{4-r}$, Si($R^2$)$_{4-r}$, N(Ar)$_{3-r}$, where r stands for 2, 3 or 4, with the proviso that r is not greater than the maximum valence of L; or L is a chemical bond, in which case q=2; the valence of the group L=q+1 here;

q is 1, 2, 3, 4, 5 or 6;

R and $R^1$ is selected on each occurrence, identically or differently, from the group consisting of H, D, F, Cl, Br, I, CN, NO$_2$, C(=O)Ar, C(=O)$R^2$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent CH$_2$ groups may be replaced by $R^2$C=C$R^2$, Si($R^2$)$_2$, C=O, C=N$R^2$, P(=O)($R^2$), SO, SO$_2$, N$R^2$, O, S or CONR$^2$ and where one or more H atoms may be replaced by D, F, Cl, Br, I, CN or NO$_2$, an aromatic ring system having 6 to 60 aromatic ring atoms, which may in each case be substituted by one or more radicals $R^2$, a heteroaromatic ring system having 5 to 60 aromatic ring atoms, which contains, as heteroaryl groups, sulfur-containing or oxygen-containing heteroaryl groups and which may be substituted by one or more radicals $R^2$, an aryloxy or heteroaryloxy group having 5 to 60 aromatic ring atoms, which may be substituted by one or more radicals $R^2$, or an aralkyl or heteroaralkyl group having 5 to 60 aromatic ring atoms, which may be substituted by one or more radicals $R^2$, where two substituents $R^1$ which are bonded in the same group Y may optionally form a mono- or polycyclic, aliphatic, aromatic or heteroaromatic ring system with one another, which may be substituted by one or more radicals $R^2$; furthermore, two adjacent radicals R may form a condensed-on benzo ring, which may be substituted by one or more radicals $R^2$;

$R^2$ is selected on each occurrence, identically or differently, from the group consisting of H, D, F, Cl, Br, I, CN, NO$_2$, C(=O)Ar, C(=O)$R^3$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent CH$_2$ groups may be replaced by $R^3$C=C$R^3$, C≡C, Si($R^3$)$_2$, C=O, C=N$R^3$, P(=O) ($R^3$), SO, SO$_2$, N$R^3$, O, S or CONR$^3$ and where one or more H atoms may be replaced by D, F, Cl, Br, I, CN or NO$_2$, an aromatic ring system having 5 to 60 aromatic ring atoms, which may in each case be substituted by one or more radicals $R^3$, an aryloxy or heteroaryloxy group having 5 to 60 aromatic ring atoms, which may be substituted by one or more radicals $R^3$, or an aralkyl or heteroaralkyl group having 5 to 60 aromatic ring atoms;

Ar is on each occurrence, identically or differently, an aromatic or heteroaromatic ring system having 5-30 aromatic ring atoms, which may be substituted by one or more non-aromatic radicals $R^3$; two radicals Ar which are bonded to the same P atom may also be bridged to one another here by a single bond or a bridge selected from N($R^3$), C($R^3$)$_2$, O or S;

$R^3$ is selected from the group consisting of H, D, F, CN, an aliphatic hydrocarbon radical having 1 to 20 C atoms or an aromatic ring system having 5 to 30 aromatic ring atoms, in which one or more H atoms may be replaced by D, F, Cl, Br, I or CN the following compound is excluded from the invention:

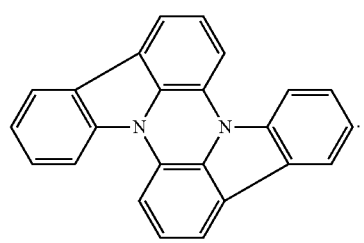 [SMILES: c1ccc2c(c1)c1cccc3c1n2c1cccc2c4ccccc4n3c21]

2. The compound according to claim 1, wherein the compound is a compound of the formula (4a) or (5a), formula (4a)
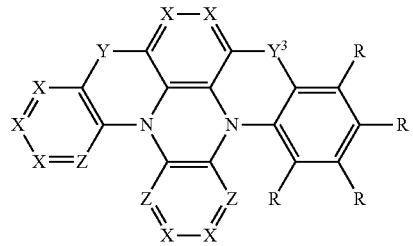

formula (5a)
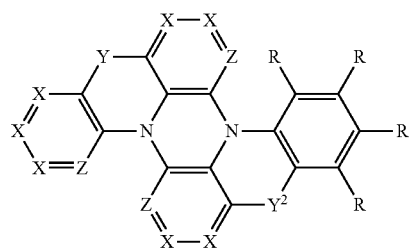

where the symbols and indices used have the meanings given in claim 1.

3. The compound according to claim 1, wherein the compound is a compound of the formulae (19a) to (22a), (24) or (25), formula (19a)
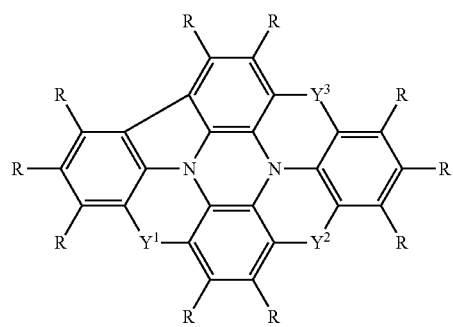

formula (20a)
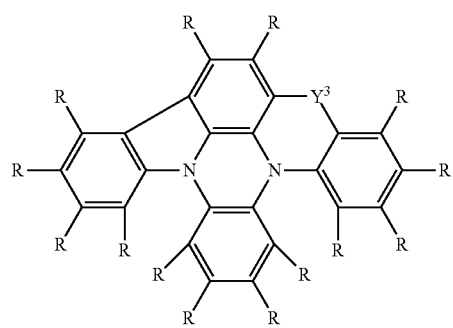

formula (21a)
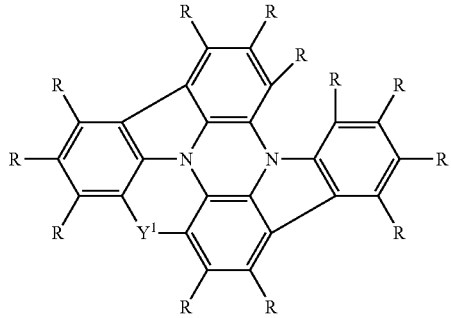

formula (22a)
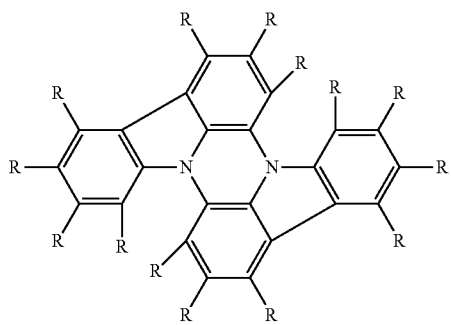

formula (24)
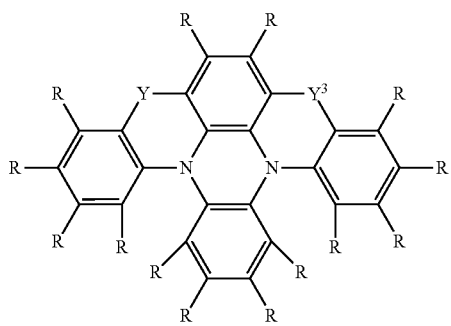

formula (25)
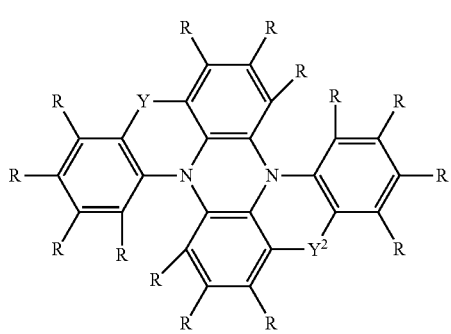

where the symbols used have the meanings given under claim 1.

4. The compound according to claim 1, wherein the compound is a compound of the formulae (19b) to (22b), (24a) or (25a), formula (19b)
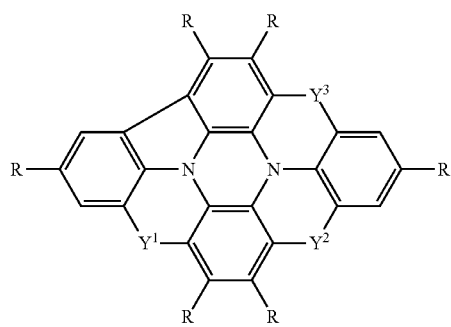
formula (20b)
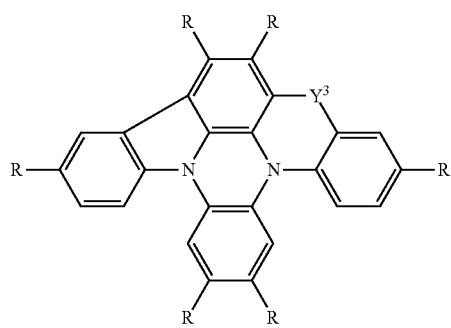
formula (21b)
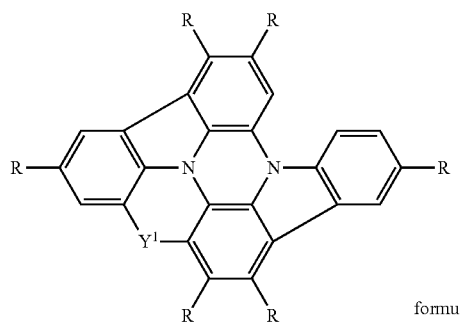
formula (22b)
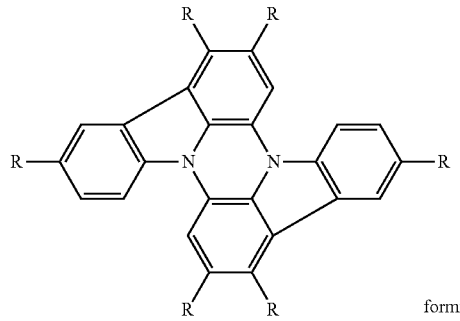
formula (24)
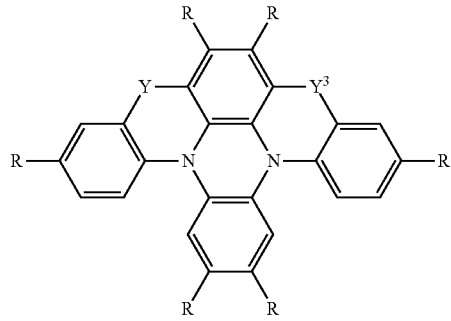
formula (25)
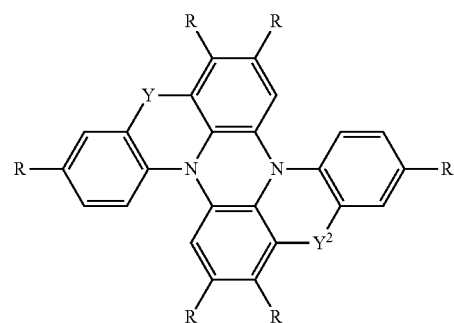
where the symbols used have the meanings given in claim 1.
5. The compound according to claim 1, wherein R, if R stands for an aromatic or heteroaromatic ring system, is selected from the groups of the formulae (26) to (58),
Formula (26)
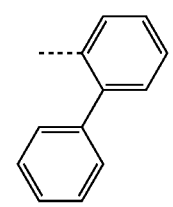
Formula (27)
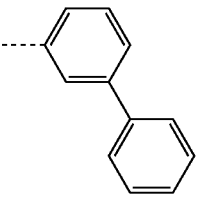
Formula (28)
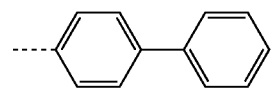
Formula (29)
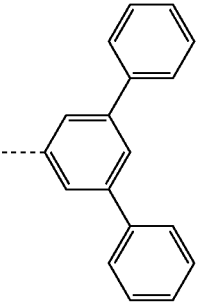
Formula (30)
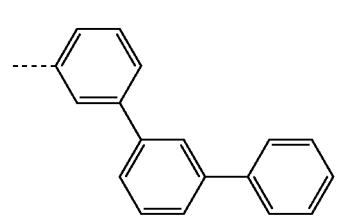

Formula (31)
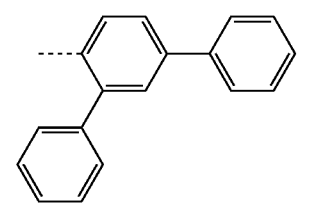
Formula (32)
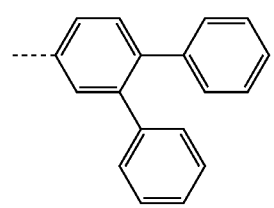
Formula (33)
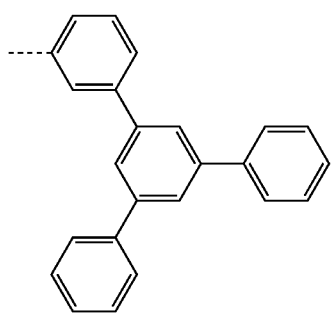
Formula (34)
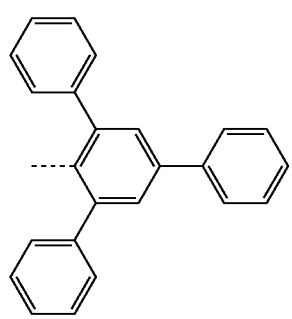
Formula (35)
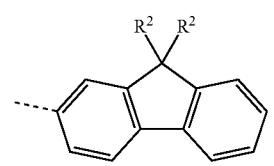
Formula (36)
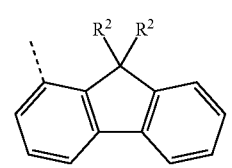
Formula (37)
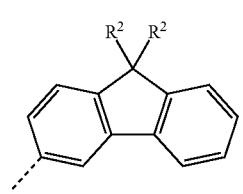
Formula (38)
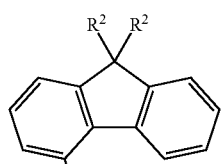
Formula (39)
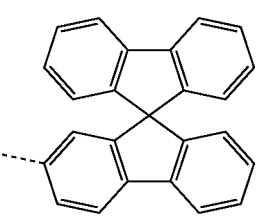
Formula (40)
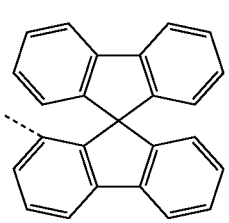
Formula (41)
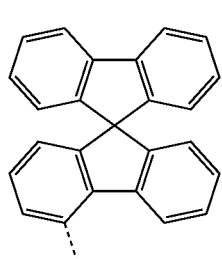
Formula (42)
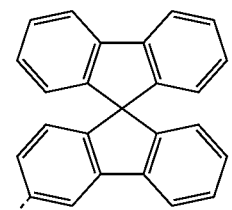
Formula (43)
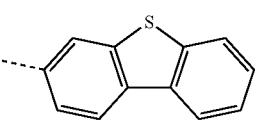
Formula (44)
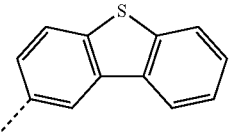
Formula (45)
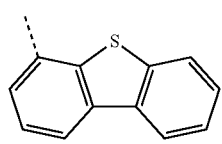

-continued

Formula (46)
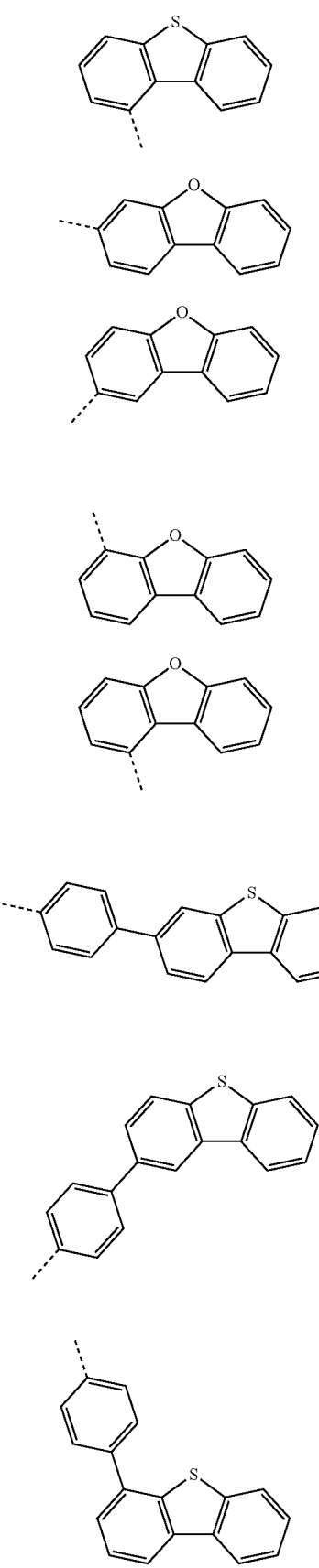

Formula (47)

Formula (48)

Formula (49)

Formula (50)

Formula (51)

Formula (52)

Formula (53)

-continued

Formula (54)
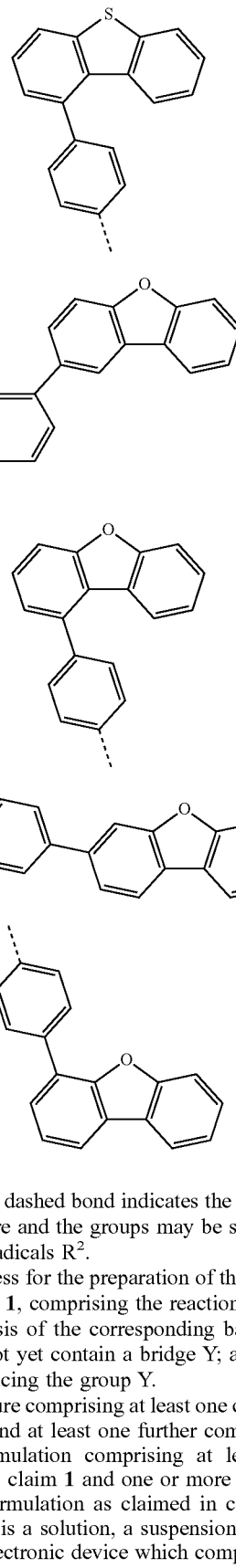

Formula (55)

Formula (56)

Formula (57)

Formula (58)

where the dashed bond indicates the bonding to the basic structure and the groups may be substituted by one or more radicals $R^2$.

6. A process for the preparation of the compound according to claim 1, comprising the reaction steps:
   a) synthesis of the corresponding basic structure which does not yet contain a bridge Y; and
   b) introducing the group Y.

7. A mixture comprising at least one compound according to claim 1 and at least one further compound.

8. A formulation comprising at least one compound according to claim 1 and one or more solvents.

9. The formulation as claimed in claim 8, wherein the formulation is a solution, a suspension or a miniemulsion.

10. An electronic device which comprises the compound according to claim 1.

11. The electronic device as claimed in claim 10, wherein the device is selected from the group consisting of organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes and "organic plasmon emitting devices".

12. An organic electroluminescent device comprising the compound according to claim 1 is employed as matrix material for fluorescent or phosphorescent emitters and/or in an electron-blocking or exciton-blocking layer and/or in a hole-transport or hole-injection layer.

* * * * *